United States Patent
Schneider et al.

(10) Patent No.: US 12,312,622 B2
(45) Date of Patent: May 27, 2025

(54) METHOD FOR PRODUCING GUANIDINO ACETIC ACID (GAA)

(71) Applicant: Evonik Operations GmbH, Essen (DE)

(72) Inventors: Frank Schneider, Halle (DE); Kay Marin, Borgholzhausen (DE); Melanie Nickolaus, Spenge (DE); Julia Tegethoff, Halle (DE); Marleen Oesterhoff, Paderborn (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/870,088

(22) PCT Filed: May 24, 2023

(86) PCT No.: PCT/EP2023/063902
§ 371 (c)(1),
(2) Date: Nov. 27, 2024

(87) PCT Pub. No.: WO2023/232584
PCT Pub. Date: Dec. 7, 2023

(65) Prior Publication Data
US 2025/0115938 A1  Apr. 10, 2025

(30) Foreign Application Priority Data
Jun. 3, 2022 (EP) ..................................... 22177256

(51) Int. Cl.
| | | |
|---|---|---|
| C12P 13/04 | (2006.01) | |
| C12N 9/06 | (2006.01) | |
| C12N 9/10 | (2006.01) | |
| C12N 9/12 | (2006.01) | |
| C12N 15/77 | (2006.01) | |
| C12P 13/10 | (2006.01) | |

(52) U.S. Cl.
CPC ............ *C12P 13/04* (2013.01); *C12N 9/0016* (2013.01); *C12N 9/1007* (2013.01); *C12N 9/1096* (2013.01); *C12N 9/1217* (2013.01); *C12N 15/77* (2013.01); *C12P 13/10* (2013.01); *C12Y 201/01002* (2013.01); *C12Y 201/04001* (2013.01); *C12Y 206/01044* (2013.01); *C12Y 207/02002* (2013.01)

(58) Field of Classification Search
None
See application file for complete search history.

(56) References Cited

U.S. PATENT DOCUMENTS

| | | |
|---|---|---|
| 11,999,982 B2 | 6/2024 | Schneider et al. |
| 12,065,677 B2 | 8/2024 | Schneider et al. |
| 2011/0257075 A1 | 10/2011 | Gastner et al. |
| 2023/0227795 A1 | 7/2023 | Schneider et al. |
| 2023/0265471 A1 | 8/2023 | Schneider et al. |

FOREIGN PATENT DOCUMENTS

| | | |
|---|---|---|
| CN | 106065411 | 11/2016 |
| WO | 2005/120246 | 12/2005 |
| WO | 2021/122400 | 6/2021 |
| WO | 2022/008276 | 1/2022 |
| WO | 2022/008280 | 1/2022 |

OTHER PUBLICATIONS

Fernandes et al., "Alteration of substrate specificity of alanine dehydrogenase", Protein Engineering, Design and Selection, vol. 28, No. 2, 2015, pp. 29-35.
Giffin et al., "ald of *Mycobacterium tuberculosis* Encodes both the Alanine Dehydrogenase and the Putative Glycine Dehydrogenase", Journal of Bacteriology, vol. 194, No. 5, Mar. 2012, pp. 1045-1054.
Ginesy et al., "Metabolic engineering of *Escherichia coli* for enhanced arginine biosynthesis", Microbial Cell Factories, vol. 14, No. 29, Mar. 7, 2015, pp. 1-11.
Guthmiller et al., "Cloning and Sequencing of Rat Kidney L-Arginine:Glycine Amidinotransferase", The Journal of Biological Chemistry, vol. 269, No. 26, Jul. 1, 1994, pp. 17556-17560.
Humm et al., "Recombinant expression and isolation of human L-arginine:glycine amidinotransferase and identification of its active-site cysteine residue", Biochem. J., vol. 322, Oct. 15, 1996, pp. 771-776.
International Search Report received for PCT Application No. PCT/EP2023/063902, mailed on Sep. 22, 2023, 8 pages.
Kameya et al., "Purification of three aminotransferases from Hydrogenobacter thermophilus TK-6—novel types of alanine or glycine aminotransferase Enzymes and catalysis", FEBS Journal, vol. 277, Feb. 2, 2010, pp. 1876-1885.
Liepman et al., "Alanine Aminotransferase Homologs Catalyze the Glutamate:Glyoxylate Aminotransferase Reaction in Peroxisomes of *Arabidopsis*", Plant Physiology, vol. 131, Jan. 2003, pp. 215-227.
Marina et al., "Carbamate kinase from Enterococcus faecalis and Enterococcus faecium Cloning of the genes, studies on the enzyme expressed in *Escherichia coli*, and sequence similarity with N-acetyl-L-gluatamate kinase", Eur. J. Biochem., vol. 253, 1998, pp. 280-291.
Muenchhoff et al., "A novel prokaryotic L-arginine:glycine amidinotransferase is involved in cylindrospermopsin biosynthesis", FEBS Journal, vol. 277, July 22, 2010, pp. 3844-3860.

(Continued)

*Primary Examiner* — Suzanne M Noakes
*Assistant Examiner* — Jae W Lee
(74) *Attorney, Agent, or Firm* — Grüneberg and Myers PLLC

(57) ABSTRACT

A microorganism is capable of producing guanidinoacetic acid (GAA) that has been improved by using a carbamate kinase. The microorganism with an improved capacity to provide L-arginine as starting material of the GAA biosynthesis by efficient recycling of ornithine improves the production process of GAA. A method for the fermentative production of GAA and a method for the fermentative production of creatine include the incorporation of the microorganism.

15 Claims, No Drawings

Specification includes a Sequence Listing.

(56) References Cited

OTHER PUBLICATIONS

Park et al., "Metabolic engineering of Corynebacterium glutamicum for L-arginine production", Nature Communications, vol. 5, No. 4618, Aug. 5, 2014, pp. 1-9.

Pátek et al., "Corynebacterium glutamicum promoters: a practical approach", Microbial Biotechnology, vol. 6, 2013, pp. 103-117.

Phogosee et al., "Bifunctional Alanine dehydrogenase from the halotolerant cyanobacterium Aphanothece halophytica: characterization and molecular properties", Archives of Microbiology, vol. 200, Jan. 29, 2018, pp. 719-727.

Sakuraba et al., "Novel Archaeal Alanine:Glyoxylate Aminotransferase from Thermococcus litoralis", Journal of Bacteriology, vol. 186, No. 16, Aug. 2004, pp. 5513-5518.

Schuffenhauer et al., "Morpholine-induced formation of L-alanine dehydrogenase activity in *Mycobaterium* strain HE5", Arch. Microbiol., vol. 171, Mar. 11, 1999, pp. 417-423.

Takada et al., "Characteristics of alanine:glyoxylate aminotransferase from *Saccharomyces cerevisiae*, a regulatory enzyme in the glyoxylate pathway of glycine and serine biosynthesis from tricarboxylic acid-cycle intermediates", Biochem. J., vol. 231, June 14, 1985, pp. 157-163.

Vančura et al., "Alanine dehydrogenase from Streptomyces fradiae Purification and Properties", Eur. J. Biochem., vol. 179, 1989, pp. 221-227.

Wang et al., "Enhanced production of L-arginine by improving carbamoyl phosphate supply in metabolically engineered Corynebacterium crenatum"; Applied Microbiology and Biotechnology, vol. 105, No. 8, Apr. 10, 2021, pp. 3265-3276.

Wang et al., "Increased expression of pyruvate carboxylase and biotin protein ligase increases lysine production in a biotin prototrophic Corynebacterium glutamicum strain", Eng. Life Sci., vol. 15, 2015, pp. 73-82.

Written Opinion received for PCT Application No. PCT/EP2023/063902, mailed on Sep. 22, 2023, 8 pages.

Yan et al., "Biosynthesis of Guanidinoacetate by Bacillus subtilis Whole-Cell Catalysis", Fermentation, vol. 8, No. 116, Mar. 7, 2022, pp. 1-11.

Yim et al., "Purification and characterization of an arginine regulatory protein, ArgR, in Corynebacterium glutamicum", J. Ind. Microbiol. Biotechnol., vol. 38, May 11, 2011, pp. 1911-1920.

Yoshida et al., "Enzymic Properties of Alanine Dehydrogenase of Bacillus Subtilis", Biochim. Biophys. Acta, vol. 96, 1965, pp. 248-262.

Zhang et al., "Reconstitution of the Ornithine Cycle with Arginine:Glycine Amidinotransferase to Engineer *Escherichia coli* into an Efficient Whole-Cell Catalyst of Guanidinoacetate", ACS Synth. Biol., vol. 9, Jul. 23, 2020, pp. 2066-2075.

U.S. Appl. No. 17/757,441, filed Jun. 15, 2022, Schneider et al.

U.S. Pat. No. 12,065,677, Aug. 20, 2024, 2023/0227795, Schneider et al.

U.S. Pat. No. 11,999,982, Jun. 4, 2024, 2023/0265471, Schneider et al.

METHOD FOR PRODUCING GUANIDINO ACETIC ACID (GAA)

CROSS-REFERENCE TO RELATED APPLICATIONS

This application is a National Stage entry under § 371 of International Application No. PCT/EP2023/063902, filed on May 24, 2023, and which claims the benefit of priority to European Patent Application No. 22177256.9, filed on Jun. 3, 2022. The content of each of these applications is hereby incorporated by reference in its entirety.

REFERENCE TO A SEQUENCE LISTING

The present application is accompanied by an XML file as a computer readable form containing the sequence listing entitled, "006200USPCT-SL-as-filed.xml", created on Oct. 2, 2024, with a file size of 47,964 bytes, the content of which is hereby incorporated by reference in its entirety.

BACKGROUND OF THE INVENTION

Field of the Invention

Guanidino acetic acid (GAA) is a colorless crystalline organic compound used as animal feed additive (e.g. WO 2005120246 A1 and US2011257075 A1). GAA is a natural precursor of creatine (e.g. Humm et al., Biochem. J. (1997) 322, 771-776). Therefore, the supplementation of GAA allows for an optimal supply of creatine in the organism.

The present invention pertains to a microorganism transformed to be capable of producing guanidinoacetic acid (GAA) and to a method for the fermentative production of GAA using such microorganism. The present invention also relates to a method for the fermentative production of creatine.

In biological systems GAA and ornithine are formed from arginine and glycine as starting materials by the catalytic action of an L-arginine: glycine-amidinotransferase (AGAT; EC 2.1.4.1). This reaction is also the first step in creatine biosynthesis.

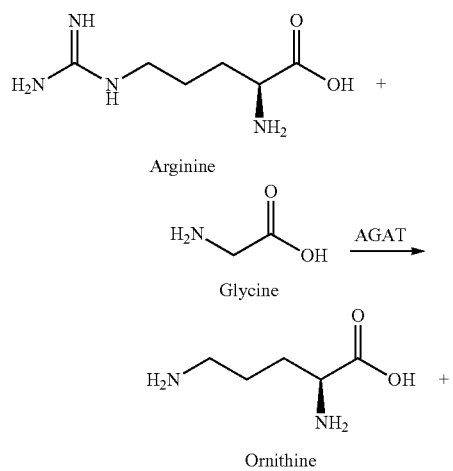

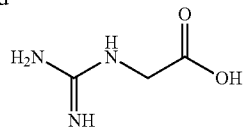

Guanidinoacetic acid (GAA)

Description of Related Art

Guthmiller et al. (J Biol Chem. 1994 Jul. 1; 269(26): 17556-60) have characterized a rat kidney AGAT by cloning and heterologously expressing the enzyme in *Escherichia coli* (*E. coli*). Muenchhoff et al. (FEBS Journal 277 (2010) 3844-3860) report the first characterization of an AGAT from a prokaryote also by cloning and heterologously expressing the enzyme in *E. coli*.

Fan Wenchao discloses a method for the production of creatine by fermentation of non-pathogenic microorganisms, such as *Corynebacterium glutamicum* (CN 106065411 A). The microorganism has the following biotransformation functions: glucose conversion to L-glutamic acid; conversion of L-glutamic acid to N-acetyl-L-glutamic acid; conversion of N-acetyl-L-glutamic acid to N-acetyl-L-glutamic acid semialdehyde; conversion of N-acetyl-L-glutamic acid semialdehyde to N-acetyl-L-ornithine; conversion of N-acetyl-L-ornithine to L-ornithine; conversion of L-ornithine to L-citrulline; conversion of L-citrulline to arginino-succinic acid; conversion of arginino-succinic acid to L-arginine; conversion of L-arginine to guanidinoacetic acid; and, finally, conversion of guanidinoacetic acid to creatine. Fan Wenchao proposes, that the microorganism overexpresses one or more enzymes selected from the group consisting of N-acetylglutamate-synthase, N-acetylornithine-δ-aminotransferase, N-acetylornithinase, ornithine-carbamoyl transferase, argininosuccinate synthetase, glycine amidino-transferase (EC: 2.1.4.1), and guanidinoacetate N-methyltransferase (EC: 2.1.1.2). The microorganism overexpresses preferably glycine aminotransferase (L-arginine: glycine amidinotransferase) and guanidinoacetate N-methyltransferase.

A microorganism capable of producing guanidinoacetic acid (GAA) was published by Zhang et al. (ACS Synth. Biol. 2020, 9, 2066-275). They designed a reconstituted the ornithine cycle in *E. coli* by introducing a heterologous AGAT from different species (e.g., *Homo sapiens, Cylindrospermopsis raciborskii, Moorea producens*) and by introducing a citrulline synthesis module (e.g. ovexpression of carAB, argF and argI) and an arginine synthesis module (e.g. overexpression of argG, argH; introduction of aspA) into *E. coli*.

Schneider and Jankowitsch (WO 2021122400 A1) propose a method to produce GAA using a microorganism having gene coding for a protein having the function of an L-arginine: glycine amidinotransferase and an increased carbamolyphosphate synthase. The carbamoyl phosphate is an important precursor for the biosynthesis of GAA but also for L-arginine and other compounds.

Several approaches for increasing the production of one of the starting materials in GAA synthesis, i.e. L-arginine, in microorganisms, particularly bacteria, are also known from literature. An overview for the metabolic engineering of *Corynebacterium glutamicum* (*C. glutamicum*) for L-arginine production is provided by Park et al. (NATURE COMMUNICATIONS|DOI: 10.1038/ncomms5618). Yim et al. (J Ind Microbiol Biotechnol (2011) 38:1911-1920) could show that inactivation of the argR, gene coding for the central repressor protein ArgR controlling the L-arginine biosynthetic pathway, by disrupting the chromosomal argR gene in *C. glutamicum* leads to an improved arginine-producing strain. Ginesy et al. (Microbial Cell Factories (2015) 14:29) report the successful engineering of *E. coli* for enhanced arginine production. Among other, they proposed the deletion of the argR repressor gene.

Wang et al. (Applied Microbiology and Biotechnology, 2021, vol. 105, pp. 3265-3276; https://doi.org/10.1007/s00253-021-11242-w) underlined that carbamoyl phosphate is essential for L-arginine production also in *Corynebacterium* sp. They showed among other that the overexpression of the carAB gene encoding a carbamoyl phosphate synthetase and the introduction of a heterologous gene (from *Enterococcus faecalis*) coding for a carbamate kinase (CK) which catalyzes synthesis of carbamoyl phosphate from inorganic ammonia, hydrogencarbonate and ATP can lead to an increase of L-arginine production. The advantage of using a carbamate kinase results from the utilization of inorganic ammonium as nitrogen source by this enzyme. In comparison to the carbamoyl phosphate synthetase, using glutamine as nitrogen source, the carbamate kinase allows a reduction of the overall energy demand for the formation of carbamoyl phosphate. Yan et al. (Fermentation 2022, vol. 8, no. 3, 7 Mar. 2022, p. 116; doi: 10.3390/fermentation8030116) disclose the biosynthesis of GAA by a whole-cell catalysis with *Bacillus subtilis* by introducing a heterologous AGAT gene into *B. subtilis*, optimizing the expression level of the AGAT gene, optimizing the natural ornithine cycle and knocking-out the first gene of the glycine degradation pathway, the glycine dehydrogenase gene gcvP.

Schneider and Jankowitsch (WO 2022008276 A1) propose to produce GAA using recombinant microorganisms comprising a gene coding for a L-arginine: glycine amidinotransferase (AGAT) and, in order to increase the production of one of the starting materials, glycine, a reduced or deleted malate synthase gene and optionally an overexpressed gene coding for a glyoxylate aminotransferase. They also disclose that the carbamate kinase (CK) may contribute to arginine production.

To increase the production of GAA using a microorganism an intracellular high amount of the starting materials arginine and/or glycine are necessary. At the same time the byproduct of the AGAT reaction, ornithine, has to be recycled to arginine efficiently in order to prevent loss of carbon and energy.

SUMMARY OF THE INVENTION

The problem underlying the present inventions is to provide a microorganism transformed to be capable for producing guanidinoacetic acid (GAA), in particular a microorganism with an improved capacity to provide L-arginine as starting material of the GAA biosynthesis by efficient recycling of ornithine, and a method for the fermentative production of GAA using such microorganism.

The problem is solved by a microorganism comprising at least one heterologous gene coding for a protein having the function of a L-arginine: glycine amidinotransferase (AGAT, e.g. EC2.1.4.1) and comprising at least one gene coding for a protein having the function of a carbamate kinase (CK, e.g. EC 2.7.2.2) and further comprising at least one gene coding for a protein having the function of a NADH-dependent amino acid dehydrogenase.

DETAILED DESCRIPTION OF THE INVENTION

A heterologous gene means that the gene has been inserted into a host organism which does not naturally have this gene. Insertion of the heterologous gene in the host is performed by recombinant DNA technology. Microorganisms that have undergone recombinant DNA technology are called transgenic, genetically modified or recombinant. A heterologous protein means a protein that is not naturally occurring in the microorganism. A homologous or endogenous gene means that the gene including its function as such or the nucleotide sequence of the gene is naturally occurring in the microorganism or is "native" in the microorganism. A homologous or a native protein means a protein that is naturally occurring in the microorganism.

In the microorganism according to the present invention the protein having the function of an L-arginine:glycine amidinotransferase (AGAT) comprises an amino acid sequence which is at least 80% identical to the amino acid sequence according to SEQ ID NO:9.

In the microorganism according to the present invention the at least one gene coding for a protein having the function of a carbamate kinase (CK, e.g. EC 2.7.2.2) may be heterologous.

In the microorganism according to the present invention the activity of the least one protein having the function of a carbamate kinase is increased compared with the respective activity in the wildtype microorganism.

Generally, increased enzyme activities in the microorganism can be achieved, for example, by mutation of the corresponding endogenous gene. A further measure to increase enzymatic activities may be to stabilize the mRNA coding for the enzymes. Increased enzyme activities in the microorganism may also be achieved by overexpression of the genes coding for the respective enzymes.

The microorganism according to the present invention may comprise at least one heterologous gene coding for a protein having the function of a carbamate kinase. In the microorganism of the present invention the at least one protein having the enzymic activity of a carbamate kinase may comprise an amino acid sequence which is at least 80% identical to the amino acid sequence according to SEQ ID NO:6.

Overexpression of a gene is generally achieved by increasing the copy number of the gene and/or by functionally linking the gene with a strong promoter and/or by enhancing the ribosomal binding site and/or by codon usage optimization of the start codon or of the whole gene or a combination comprising a selection of all methods mentioned above.

A promoter is a DNA sequence consisting of about 40 to 50 base pairs and which constitutes the binding site for an RNA polymerase holoenzyme and the transcriptional start point, whereby the strength of expression of the controlled polynucleotide or gene can be influenced. Generally, it is possible to achieve an overexpression or an increase in the expression of genes in bacteria by selecting strong promoters, for example by replacing the original promoter with strong, native (originally assigned to other genes) promoters or by modifying certain regions of a given, native promoter (for example its so-called −10 and −35 regions) towards a consensus sequence, e.g. as taught by M. Patek et al. (Microbial Biotechnology 6 (2013), 103-117) for *C. gluta-*

*micum*. An example for a "strong" promoter is the superoxide dismutase (sod) promoter ("Psod"; Z. Wang et al., Eng. Life Sci. 2015, 15, 73-82). A "functional linkage" is understood to mean the sequential arrangement of a promoter with a gene, which leads to a transcription of the gene.

In a particular embodiment of the present invention the gene coding for a protein having the function of a carbamate kinase is functionally linked to a strong promoter. Preferably, the promoter is the superoxide dismutase (sod) promoter ("Psod").

In the microorganism according to the present invention the protein having the function of a NADH-dependent amino acid dehydrogenase may be a heterologous protein.

NADH depending amino acid dehydrogenases (AaDH) catalyse the amination reaction of a keto acid to L-amino acid; the NADH depending amino acid dehydrogenases are important for the assimilation or dissimilation of ammonium in a cell.

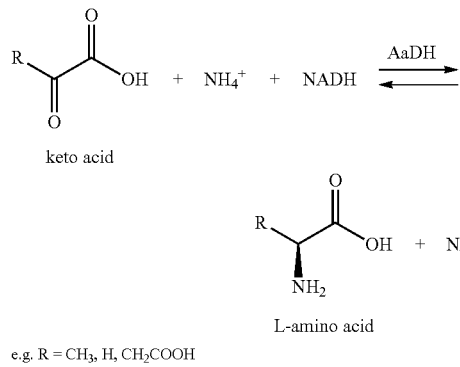

Since most of these amino acid dehydrogenases can use different a-keto acids as substrate, they are often annotated with different EC numbers. However, all these amino acid dehydrogenases have in common that they assimilate ammonium, or, in case of the reverse reaction, dissimilate ammonium.

Examples for different amino acid dehydrogenases are the following:

Reaction EC 1.4.1.1: Alanine Dehydrogenase:

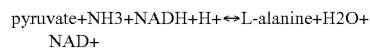

Reaction EC 1.4.1.10: Glycine Dehydrogenase:

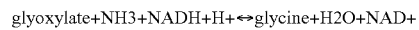

Reaction EC 1.4.1.21: Aspartate Dehydrogenase:

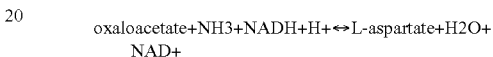

Several NADH depending amino acid dehydrogenase (AaDH) Proteins are known in literature which accept a broad range of substrates and can therefore often aminate several different keto acids to the corresponding amino acids. (Fernandes et al. Protein Engineering, Design & Selection, 2015, vol. 28 no. 2, pp. 29-35; Giffin et al., Journal of Bacteriology, 2012, vol. 194 no. 5, pp. 1045-1054; Phogosee et al., Archives of Microbiology, 2018 vol. 200 pp. 719-727; Schuffenhauer et al. 1999, vol. 171, pp 417-423; Vancura et al. Eur J Biochem 1989, vol. 179, pp. 221-227, Yoshida and Freese, Biochim. Biophys. Acta, 1965, vol. 96, pp 248-262)

Therefore, no clear link of the reaction to an EC number exists. Table 1 shows some examples:

TABLE 1

Examples for NADH depending amino acid dehydrogenase (AaDH) Proteins

| Reaction | AaDH *Mycobacterium tuberculosis* | AaDH *Mycobacterium smegmatis* | AaDH *Bacillus subtilis* | AaDH *Streptomyces fradiae* | AaDH *Aphanothece halophytica* |
|---|---|---|---|---|---|
| Pyruvat->L-Alanin | yes (1) | yes (3) | yes (4) | yes (5) | yes (6) |
| L-Alanin->Pyruvat | yes (1) | yes (3) | yes (4) | yes (5) | yes (6) |
| Glyoxylat->Glycin | yes (1) | yes (3) | yes (4) | no (5) | yes (6) |
| Oxalacetat->Aspartat | yes (1) | yes (3) | no data | yes (5) | no data |
| Hydroxypyruvat -> Serin | yes (1) | no data | yes (4) | no data | no data |
| Methylglyoxal -> Aminoaceton | yes (1) | no data | no data | no data | no data |
| 4-Hydroxy-2-oxobutyrat -> L-Homoserin | yes (2) | no data | no data | no data | no data |
| 2-Oxobutyrate -> 2-aminobutyrate | no data | yes (3) | yes (4) | yes (5) | no data |
| Literature | (1) Giffin, 2012 (2) Fernandes, 2015 | (3) Schuffenhauer, 1999 | (4) Yoshida, 1965 | (5) Vancura, 1989 | (6) Phogosee, 2019 |

In the microorganism according to the present invention the at least one protein having the function of a NADH-dependent amino acid dehydrogenase may be selected from the group consisting of alanine dehydrogenase (EC 1.4.1.1), glycine dehydrogenase (EC 1.4.1.10) and aspartate dehydrogenase (EC 1.4.1.21).

In the microorganism of the present invention the activity of the at least one NADH-dependent amino acid dehydrogenase may be increased compared with the respective activity in the wildtype microorganism.

The at least one protein having the function of a NADH-dependent amino acid dehydrogenase is preferably heterologous.

The at least one NADH-dependent amino acid dehydrogenase comprised in the microorganism according to the present invention may be selected from the group consisting of alanine dehydrogenase (EC 1.4.1.1), glycine dehydrogenase (EC 1.4.1.10) and aspartate dehydrogenase (EC 1.4.1.21).

In the microorganism of the present invention the protein having the function of a NADH-dependent amino acid dehydrogenase may comprise an amino acid sequence which is at least 80% identical to the amino acid sequence according to SEQ ID NO: 13, according to SEQ ID NO:21, according to SEQ ID NO:22, according to SEQ ID NO:23 or according to SEQ ID NO:24.

The microorganism of the present invention may further comprise at least one gene coding for a protein having the function of a glyoxylate aminotransferase.

Several glyoxylate amino transferases are known and vary in their substrate specificity with respect to the amino donor (cf. e.g. Kameya et al. FEBS Journal 277 (2010) 1876-1885; Liepman and Olsen, Plant Physiol. Vol. 131, 2003, 215-227; Sakuraba et al., JOURNAL OF BACTERIOLOGY, August 2004, p. 5513-5518; Takada and Noguchi, Biochem. J. (1985) 231, 157-163). Since most of these glyoxylate aminotransferase can use different amino acids as amino donors, they are often annotated with different EC numbers. However, all these aminotransferases have in common that they use glyoxylate as acceptor molecule, or, in case of the reverse reaction, glycine as donor molecule. Examples for a protein having the function of a glyoxylate aminotransferase are the following:

Glycine Transaminase (EC 2.6.1.4) Catalyzes the Reaction:

L-glutamate+glyoxylate⇌alpha-ketoglutarate+glycine.

Glycine: Oxaloacetate Transaminase (EC 2.6.1.35) Catalyzes the Reaction:

L-aspartate+glyoxylate⇌oxaloacetate+glycine.

Alanine: Glyoxylate Transaminase (EC 2.6.1.44) Catalyzes the Reaction:

L-alanine+glyoxylate⇌pyruvate+glycine.

Serine: Glyoxylate Transaminase (EC 2.6.1.45) Catalyzes the Reaction:

L-serine+glyoxylate⇌3-hydroxy-pyruvate+glycine.

Methionine: Glyoxylate Transaminase (EC 2.6.1.73) Catalyzes the Reaction:

L-methionine+glyoxylate⇌4-(methylsulfanyl)-2-keto-butanoate+glycine.

The Aromatic Amino Acid: Glyoxylate Transaminase (EC 2.6.1.60) Catalyzes the Reaction:

aromatic amino acid+glyoxylate⇌aromatic keto-acid+glycine.

Kynurenine: Glyoxylate Transaminase (EC 2.6.1.63) Catalyzes the Reaction:

kynurenine+glyoxylate⇌4-(2-aminophenyl)-2,4-diketo-butanoate+glycine.

(S)-Ureido-Glycine: Glyoxylate Transaminase (EC 2.6.1.112) Catalyzes the Reaction:

(S)-ureido-glycine+glyoxylate⇌N-carbamoyl-2-keto-glycine+glycine.

In a further embodiment of the present invention the enzymic activity of the at least one protein having the function of a glyoxylate aminotransferase is increased compared to the respective enzymic activity in the wildtype microorganism.

The at least one protein having the function of a glyoxylate aminotransferase is preferably heterologous.

In a particular embodiment of the present invention the at least one protein having the function of a glyoxylate aminotransferase is a glycin:glyoxylate aminotransferase.

In the microorganism of the present invention the protein having the enzymic activity of a glyoxylate aminotransferase may comprise an amino acid sequence which is at least 80% identical to the amino acid sequence according to SEQ ID NO: 16, according to SEQ ID NO: 19 or according to SEQ ID NO:20.

The microorganism according to the present invention may have an increased ability to produce L-arginine from L-ornithine compared with the ability of the wildtype microorganism.

In the context of the present invention, a microorganism having an increased ability to produce L-arginine means a microorganism producing L-arginine in excess of its own need. Examples for such L-arginine producing microorganisms are e.g. *C. glutamicum* ATCC 21831 or those disclosed by Park et al. (NATURE COMMUNICATIONS|DOI: 10.1038/ncomms5618) or by Ginesy et al. (Microbial Cell Factories (2015) 14:29). In contrast to formerly described microorganisms having an increased ability to produce L-arginine, L-arginine excretion is not necessary in strains for GAA production since arginine is utilized inside the cell in the framework of the present invention for GAA production.

In a further embodiment the microorganism according to the present invention the expression of an argR gene coding for the arginine responsive repressor protein ArgR is attenuated compared to the expression of the argR gene in the wildtype microorganism. Alternatively, the argR gene is deleted The microorganism of the present invention may belong to the genus *Corynebacterium*, to the genus *Bacillus* (Yan, K., et al. (2022). "Biosynthesis of Guanidinoacetate by *Bacillus subtilis* Whole-Cell Catalysis." Fermentation 8(3): 116), to the genus Enterobacteriaceae or to the genus *Pseudomonas*.

In a particular embodiment of the present invention the microorganism is *Corynebacterium glutamicum* (*C. glutamicum*) or *Escherichia coli* (*E. coli*).

The present invention further concerns a method for the fermentative production of guanidino acetic acid (GAA), comprising the steps of a) cultivating the microorganism according to the present invention in a medium, and b) accumulating GAA in the medium to form a GAA containing fermentation broth.

Preferably, the method further comprises isolating GAA from the GAA containing fermentation broth.

In a particular embodiment the microorganism of the present invention further comprises a gene coding for an enzyme having the activity of a guanidinoacetate N-methyltransferase. The gene coding for an enzyme having the activity of a guanidinoacetate N-methyltransferase may be overexpressed.

The present invention also concerns a method for the fermentative production of creatine, comprising the steps of a) cultivating the microorganism according to the present invention further comprising a gene coding for an enzyme having the activity of a guanidinoacetate N-methyltransferase in a suitable medium under suitable conditions, and b) accumulating creatine in the medium to form a creatine containing fermentation broth.

Preferably, the method further comprises isolating creatine from the creatine containing fermentation broth. creatine may be extracted from fermentation broth by isoelectric point method and/or ion exchange method. Alternatively, creatine can be further purified by a method of recrystallization in water.

EXPERIMENTAL SECTION

A) MATERIALS and METHODS

Chemicals

Kanamycin solution from *Streptomyces kanamyceticus* was purchased from Sigma Aldrich (St. Louis, USA, Cat. no. K0254). If not stated otherwise, all other chemicals were purchased analytically pure from Merck (Darmstadt, Germany), Sigma Aldrich (St. Louis, USA) or Carl-Roth (Karlsruhe, Germany).

Cultivation for Cell Proliferation

If not stated otherwise, cultivation/incubation procedures were performed as follows herewith:
  a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 30° C. and 200 rpm.
  b. LB agar (MILLER) from Merck (Darmstadt, Germany, Cat. no. 110283) was used for cultivation of *E. coli* strains on agar plates. The agar plates were incubated at 30° C. in an INCU-Line® mini incubator from VWR (Radnor, USA).
  c. Brain heart infusion broth (BHI) from Merck (Darmstadt, Germany, Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 30° C. and 200 rpm.
  d. Brain heart agar (BHI-agar) from Merck (Darmstadt, Germany, Cat. no. 113825) was used for cultivation of *C. glutamicum* strains on agar plates. The agar plates were incubated at 30° C. in an incubator from Heraeus Instruments with Kelvitron® temperature controller (Hanau, Germany).
  e. For cultivating *C. glutamicum* after electroporation, BHI-agar (Merck, Darmstadt, Germany, Cat. no. 113825) was supplemented with 134 g/l sorbitol (Carl Roth GmbH+Co. KG, Karlsruhe, Germany), 2.5 g/l yeast extract (Oxoid/ThermoFisher Scientific, Waltham, USA, Cat. no. LP0021) and 25 mg/l kanamycin. The agar plates were incubated at 30° C. in an incubator from Heraeus Instruments with Kelvitron® temperature controller (Hanau, Germany).

Determining Optical Density of Bacterial Suspensions
  a. The optical density of bacterial suspensions in shake flask cultures was determined at 600 nm (OD600) using the Bio-Photometer from Eppendorf AG (Hamburg, Germany).
  b. The optical density of bacterial suspensions produced in the Wouter Duetz (WDS) micro fermentation system (24-Well Plates) was determined at 660 nm (OD660) with the GENios™ plate reader from Tecan Group AG (Männedorf, Switzerland).

Centrifugation
  a. Bacterial suspensions with a maximum volume of 2 ml were centrifuged in 1.5 ml or 2 ml reaction tubes (e.g. Eppendorf Tubes® 3810X) using an Eppendorf 5417 R benchtop centrifuge (5 min. at 13.000 rpm).
  b. Bacterial suspensions with a maximum volume of 50 ml were centrifuged in 15 ml or 50 ml centrifuge tubes (e.g. Falcon™ 50 ml Conical Centrifuge Tubes) using an Eppendorf 5810 R benchtop centrifuge for 10 min. at 4.000 rpm.

DNA Isolation

Plasmid DNA from *E. coli* cells was isolated using the QIAprep Spin Miniprep Kit from Qiagen (Hilden, Germany, Cat. No. 27106) according to the instructions of the manufacturer.

Polymerase Chain Reaction (PCR)

PCR with a proof reading (high fidelity) polymerase was used to amplify a desired segment of DNA for sequencing or DNA assembly cloning. Non-proof-reading polymerase Kits were used for determining the presence or absence of a desired DNA fragment directly from *E. coli* or *C. glutamicum* colonies.
  a. The Phusion® High-Fidelity DNA Polymerase Kit (Phusion Kit) from New England BioLabs Inc. (Ipswich, USA, Cat. No. M0530) was used for template-correct amplification of selected DNA regions according to the instructions of the manufacturer (see Table 2).

TABLE 2

Thermocycling conditions for PCR with Phusion ® High-Fidelity DNA Polymerase Kit from New England BioLabs Inc.
PCR Program

| Step | Time [min.:sec.] | T [° C.] | Description |
|---|---|---|---|
| 1 | 00:30 | 98 | Initial denaturation step |
| 2 | 00:05 | 98 | Denaturation step |
| 3 | 00:30 | 60 | Annealing step |
| 4 | 30 sec. per kb DNA | 72 | Elongation step |
|   |   |   | Repeat step 2 to 4: 35 x |
| 5 | 05:00 | 72 | Final elongation step |
| 6 | Hold | 4 | Cooling step | b. Taq PCR Core Kit (Taq Kit) from Qiagen (Hilden, Germany, Cat. No. 201203) was used to amplify a desired segment of DNA to confirm its presence. The kit was used according to the instructions of the manufacturer (see Table 3).

TABLE 3

Thermocycling conditions for PCR with
Taq PCR Core Kit (Taq Kit) from Qiagen.
PCR Program

| Step | Time [min.:sec.] | T [° C.] | Description |
|---|---|---|---|
| 1 | 05:00 | 94 | Initial denaturation step |
| 2 | 00:30 | 94 | Denaturation step |
| 3 | 00:30 | 52 | Annealing step |
| 4 | 1 min. per kb DNA | 72 | Elongation step |
| | | | Repeat step 2 to 4: 35 x |
| 5 | 04:00 | 72 | Final elongation step |
| 6 | Hold | 4 | Cooling step | c. SapphireAmp® Fast PCR Master Mix (Sapphire Mix) from Takara Bio Inc (Takara Bio Europe S.A.S., Saint-Germain-en-Laye, France, Cat. No. RR350A/B) was used as an alternative to confirm the presence of a desired segment of DNA in cells taken from *E. coli* or *C. glutamicum* colonies according to the instructions of the manufacturer (see Table 4).

TABLE 4

Thermocycling conditions for PCR with SapphireAmp ®
Fast PCR Master Mix (Sapphire Mix) from Takara Bio Inc.
PCR Program

| Step | Time [min.:sec.] | T [° C.] | Description |
|---|---|---|---|
| 1 | 01:00 | 94 | Initial denaturation step |
| 2 | 00:05 | 98 | Denaturation step |
| 3 | 00:05 | 55 | Annealing step |
| 4 | 10 sec. per kb DNA | 72 | Elongation step |
| | | | Repeat step 2 to 4: 30 x |
| 5 | 04:00 | 72 | Final elongation step |
| 6 | Hold | 4 | Cooling step | d. All oligonucleotide primers were synthesized by Eurofins Genomics GmbH (Ebersberg, Germany).

e. As PCR template either a suitably diluted solution of isolated plasmid DNA or of total DNA isolated from a liquid culture or the total DNA contained in a bacterial colony (colony PCR) was used. For said colony PCR the template was prepared by taking cell material with a sterile toothpick from a colony on an agar plate and placing the cell material directly into the PCR reaction tube. The cell material was heated for 10 sec. with 800 W in a microwave oven type Mikrowave & Grill from SEVERIN Elektrogeräte GmbH (Sundern, Germany) and then the PCR reagents were added to the template in the PCR reaction tube.

f. All PCR reactions were carried out in PCR cyclers type Mastercycler or Mastercycler *nexus* gradient from Eppendorf AG (Hamburg, Germany).

Restriction Enzyme Digestion of DNA

For restriction enzyme digestions either "FastDigest restriction endonucleases (FD)" (ThermoFisher Scientific, Waltham, USA) or restriction endonucleases from New England BioLabs Inc. (Ipswich, USA) were used. The reactions were carried out according to the instructions of the manufacturer's manual.

Determining the Sizes of DNA Fragments a. The sizes of small DNA fragments (<1000 bps) were usually determined by automatic capillary electrophoresis using the QIAxcel from Qiagen (Hilden, Germany).

b. If DNA fragments needed to be isolated or if the DNA fragments were >1000 bps DNA was separated by TAE agarose gel electrophoresis and stained with GelRed® Nucleic Acid Gel Stain (Biotium, Inc., Fremont, Canada). Stained DNA was visualized at 302 nm.

Purification of PCR Amplificates and Restriction Fragments

PCR amplificates and restriction fragments were cleaned up using the QIAquick PCR Purification Kit from Qiagen (Hilden, Germany; Cat. No. 28106), according to the manufacturer's instructions. DNA was eluted with 30 µl 10 mM Tris*HCl (pH 8.5).

Determining DNA Concentration

DNA concentration was measured using the NanoDrop Spectrophotometer ND-1000 from PEQLAB Biotechnologie GmbH, since 2015 VWR brand (Erlangen, Germany).

Assembly Cloning

Plasmid vectors were assembled using the "NEBuilder HiFi DNA Assembly Cloning Kit" purchased from New England BioLabs Inc. (Ipswich, USA, Cat. No. E5520). The reaction mix, containing the linear vector and at least one DNA insert, was incubated at 50° C. for 60 min. 0.5 µl of Assembly mixture was used for each transformation experiment.

Chemical Transformation of *E. coli*

For plasmid cloning, chemically competent "NEB® Stable Competent *E. coli* (High Efficiency)" (New England BioLabs Inc., Ipswich, USA, Cat. No. C3040) were transformed according to the manufacturer's protocol. Successfully transformed cells were selected on LB agar supplemented with 25 mg/l kanamycin.

Transformation of *C. glutamicum*

Transformation of *C. glutamicum* with plasmid-DNA was conducted via electroporation using a "Gene Pulser Xcell" (Bio-Rad Laboratories GmbH, Feldkirchen, Germany) as described by Ruan et al. (2015). Electroporation was performed in 1 mm electroporation cuvettes (Bio-Rad Laboratories GmbH, Feldkirchen, Germany) at 1.8 kV and a fixed time constant set to 5 ms. Transformed cells were selected on BHI-agar containing 134 g/l sorbitol, 2.5 g/l Yeast Extract and 25 mg/l kanamycin.

Determining Nucleotide Sequences

Nucleotide sequences of DNA molecules were determined by Eurofins Genomics GmbH (Ebersberg, Germany) by cycle sequencing, using the dideoxy chain termination method of Sanger et al. (Proceedings of the National Academy of Sciences USA 74, 5463-5467, 1977). Clonemanager Professional 9 software from Scientific & Educational Software (Denver, USA) was used to visualize and evaluate the sequences as well as for in silico assembly of sequences.

Glycerol Stocks of *E. coli* and *C. glutamicum* Strains

For long time storage of *E. coli*- and *C. glutamicum* strains glycerol stocks were prepared. Selected *E. coli* clones were cultivated in 10 ml LB medium supplemented with 2 g/l glucose. Selected *C. glutamicum* clones were cultivated in 10 ml twofold concentrated BHI medium supplemented with 2 g/l glucose. Media for growing plasmid containing *E. coli*- and *C. glutamicum* strains were supplemented with 25 mg/l kanamycin. The medium was contained in 100 ml Erlenmeyer flasks with 3 baffles. It was inoculated with a loop of cells taken from a colony. The culture was then incubated for 18 h at 30° C. and 200 rpm. After said incubation period 1.2 ml 85% (v/v) sterile glycerol were added to the culture. The obtained glycerol containing cell suspension was then aliquoted in 2 ml portions and stored at −80° C.

GAA Production in Millilitre-Scale Cultivations

The millilitre-scale cultivation system according to Duetz (2007) was used to assess the GAA-production of the strains. For this purpose, 24-deepwell microplates (24 well WDS plates) from EnzyScreen BV (Heemstede, Netherlands, Cat. no. CR1424) filled with 2.5 ml medium per well were used.

Precultures of the strains were done in 10 ml seed medium (SM). The medium was contained in a 100 ml Erlenmeyer flask with 3 baffles. It was inoculated with 100 µl of a glycerol stock culture and the culture was incubated for 24 h at 30° C. and 200 rpm. The composition of the seed medium (SM) is shown in Table 5.

TABLE 5

Seed medium (SM)

| Components | Concentration (g/l) |
| --- | --- |
| Yeast extract FM902 (Angel Yeast Co., LTD, Hubei, P.R. China) | 10 |
| Urea | 1.5 |
| $KH_2PO_4$ | 0.5 |
| $K_2HPO_4$ | 0.5 |
| $MgSO_4 * 7 H_2O$ | 1 |
| Biotin | 0.0001 |
| Thiamine hydrochloride | 0.0001 |
| $FeSO_4 * 7 H_2O$ | 0.01 |
| $MnSO_4 * H_2O$ | 0.01 |
| Glucose | 20 |
| Kanamycin | 0.025 |
| pH = 7.0 | |

After said incubation period the optical densities OD600 of the precultures were determined. The volume, needed to inoculate 2.5 ml of production medium (PM) to an OD600 of 0.1, was sampled from the preculture, centrifuged (1 min at 8000 g) and the supernatant was discarded. Cells were then resuspended in 100 µl of production medium.

The main cultures were started by inoculating the 2.4 ml production medium (PM) containing wells of the 24 Well WDS-Plate with each 100 µl of the resuspended cells from the precultures. The composition of the production medium (PM) is shown in Table 6.

TABLE 6

Production medium (PM)

| Components | Concentration (g/l) |
| --- | --- |
| 3-(N-morpholino)propanesulfonic acid (MOPS) | 40 |
| Yeast extract FM902 (Angel Yeast Co., LTD, Hubei, P.R. China) | 1.5 |
| $(NH_4)_2SO_4$ | 10 |
| $NH_4Cl$ | 15 |
| Trisodium citrate * 2 $H_2O$ | 10 |
| Urea | 1 |
| $KH_2PO_4$ | 0.5 |
| $K_2HPO_4$ | 0.5 |
| Ammonium acetate | 7.7 |
| $MgSO_4 * 7 H_2O$ | 1 |
| Biotin | 0.0001 |
| Thiamine hydrochloride | 0.0001 |
| $FeSO_4 * 7 H_2O$ | 0.01 |
| $MnSO_4 * H_2O$ | 0.01 |
| $ZnSO_4 * 7 H_2O$ | 0.00002 |
| $CuSO_4 * 5 H_2O$ | 0.0004 |
| Antifoam XFO-2501 (Ivanhoe Industries Inc., Zion, USA) | 0.5 |
| Glucose | 40 |
| L-Arginine | 1.9 |
| Kanamycin | 0.025 |
| pH = 7.2 | |

The main cultures were incubated for 72 h at 30° C. and 225 rpm in an Infors HT Multitron standard incubator shaker from Infors GmbH (Bottmingen, Switzerland) until complete consumption of glucose. The glucose concentration in the suspension was analysed with the blood glucose-meter OneTouch Vita® from LifeScan (Johnson & Johnson Medical GmbH, Neuss, Germany).

After cultivation the culture suspensions were transferred to a deep well microplate. A part of the culture suspension was suitably diluted to measure the OD600. Another part of the culture was centrifuged and the concentration of GAA in the supernatant was analyzed as described below.

B) Examples

Example 1: Cloning of the Plasmid pK18mobsacB_DargR for the Genomic Deletion of the Gene argR C. glutamicum To raise intracellular L-Arginine formation and L-Arginine recycling from L-Omithine, the gene argR coding for the central repressor protein ArgR controlling the L-arginine biosynthetic pathway was to be deleted. Therefore, the plasmid pK18mobsacB_DargR was constructed as follows. Plasmid pK18mobsacB (Schäfer, 1994; Genbank accession FJ437239) was digested using restriction endonuclease XbaI and the linearized vector DNA (5721 bps) was purified using the "QIAquick Gel Extraction Kit".

For constructing the insert, two DNA fragments were created by high fidelity PCR with the following pairs of primers (using DNA of ATCC13032 as a template):

DargR_lf(SEQ ID NO:1),+DargR_lr(SEQ ID NO:2)= left homology arm(983 bps)

DargR_rf(SEQ ID NO:3),+DargR_rr(SEQ ID NO:4)= left homology arm(984 bps)

The PCR products were purified using the "QIAquick PCR Purification Kit".

The linearized plasmid and the PCR products were assembled using the "NEBuilder HiFi DNA Assembly Cloning Kit". The assembly product was transformed into "NEB Stable Competent *E. coli* (High Efficiency)" and cells were grown on LB agar containing 25 mg/l kanamycin. A proper plasmid clone was identified by restriction digestion and DNA sequencing. The resulting plasmid was named pK18mobsacB_DargR.

Example 2: Chromosomal Deletion of the Gene argR in ATCC13032

*C. glutamicum* ATCC13032 (Kinoshita S, Udaka S, Shimono M., J. Gen. Appl. Microbiol. 1957; 3(3):193-205), the *Corynebacterium glutamicum* Type Strain/Wildtype, is commercially available at the American Type Culture Collection (ATCC) or at the DSMZ-German Collection of Microorganisms and Cell Cultures GmbH under the deposit no. DSM 20300.

For deleting the argR gene, plasmid pK18mobsacB_DargR was transformed into *C. glutamicum* ATCC13032 by electroporation. Chromosomal integration (resulting from a first recombination event) was selected by plating on BHI agar supplemented with 134 g/l sorbitol, 2.5 g/l yeast extract and 25 mg/l kanamycin. The agar plates were incubated for 48 h at 33° C.

Individual colonies were transferred onto fresh agar plates (with 25 mg/l kanamycin) and incubated for 24 h at 33° C. Liquid cultures of these clones were cultivated for 24 h at 33° C. in 10 ml BHI medium contained in 100 ml Erlenmeyer flasks with 3 baffles. To isolate clones that have encountered a second recombination event, an aliquot was taken from each liquid culture, suitably diluted and 100 µl were plated on BHI agar supplemented with 10% saccharose. The agar plates were incubated for 48 h at 33° C. Colonies growing on the saccharose containing agar plates were then examined for kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined by PCR and DNA sequencing. The resulting strain having a deleted argR gene was named ATCC13032_DargR.

Example 3: Cloning of the Plasmid pK18mobsacB_CK for the Genomic Integration of the Carbamate Kinase (CK, EC 2.7.2.2) Gene Derived from *Enterococcus faecalis* ATCC 29212 into *C. glutamicum*

The coding sequence arcC of *Enterococcus faecalis* ATCC 29212 codes for a carbamate kinase (Marina et al., Eur J Biochem. 1998 Apr. 1; 253(1):280-91. doi: 10.1046/j.1432-1327.1998.2530280.x; Genbank accession AJ223332, SEQ ID NO:5). SEQ ID NO:6 shows the derived amino acid sequence (Genbank accession CAA11271).

Using the software tool "Codon Optimization Tool" (Integrated DNA Technologies Inc., Coralville, Iowa, USA) the coding sequence was optimized for the codon usage of *C. glutamicum*. The resulting optimized coding sequence was named CK.

With the optimized coding sequence, a DNA fragment for the genomic integration in *C. glutamicum* between the genes NCgl0291 and NCgl0292 was designed. It consists of the following elements: a BsaI restriction site, a homologous sequence for assembly cloning into pK18mobsacB (Schäfer, 1994; Genbank accession FJ437239), a left homologous arm for integration downstream of NCgl0291, the strong sod-promotor from *C. glutamicum*, the optimized CK gene, the BioBricks Terminator BBa_B1006, a right homologous arm for genomic integration, a second homologous sequence for assembly cloning and a BsaI site. The resulting DNA sequence was named CK-insert (SEQ ID NO:7). It was ordered for gene synthesis from Invitrogen/Geneart (Thermo Fisher Scientific, Waltham, USA) and it was delivered as part of a cloning plasmid with an ampicillin resistance gene.

The cloning plasmid containing the CK-insert was digested using the restriction endonuclease BsaI and the DNA was purified with the "QIAquick PCR Purification Kit".

The plasmid pK18mobsacB was digested using the restriction endonuclease SmaI and the DNA was purified with the "QIAquick PCR Purification Kit".

The DNA of both digested plasmids was joined, and the matching sequence ends were assembled using the "NEBuilder HiFi DNA Assembly Cloning Kit". The assembly product was transformed into "NEB Stable Competent *E. coli* (High Efficiency)" and cells were grown on LB agar containing 25 mg/l kanamycin. A proper plasmid clone was identified by restriction digestion and DNA sequencing. The resulting plasmid was named pK18mobsacB_CK.

Example 4: Integration of the Carbamate Kinase Gene CK into the Genome of *C. glutamicum*

For the genomic integration of the carbamate kinase gene CK into *C. glutamicum* ATCC13032 and ATCC13032_DargR, the strains were transformed by plasmid pK18mobsacB_CK using electroporation. Chromosomal integration (resulting from a first recombination event) was selected by plating on BHI agar supplemented with 134 g/l sorbitol, 2.5 g/l yeast extract and 25 mg/l kanamycin. The agar plates were incubated for 48 h at 33° C.

Individual colonies were transferred onto fresh agar plates (with 25 mg/l kanamycin) and incubated for 24 h at 33° C. Liquid cultures of these clones were cultivated for 24 h at 33° C. in 10 ml BHI medium contained in 100 ml Erlenmeyer flasks with 3 baffles. To isolate clones that have encountered a second recombination event, an aliquot was taken from each liquid culture, suitably diluted and 100 µl were plated on BHI agar supplemented with 10% saccharose. The agar plates were incubated for 48 h at 33° C. The colonies growing on the saccharose containing agar plates were then examined for kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined by PCR and DNA sequencing for the appropriate integration of the CK gene. The resulting strains were named ATCC13032_CK and ATCC13032_DargR_CK, respectively.

TABLE 7

List of strains

| Strain | Comment |
| --- | --- |
| ATCC13032 | *Corynebacterium glutamicum* wild type strain (Kinoshita et al., 1957*) |
| ATCC13032_DargR | Chromosomal deletion of argR in *C. glutamicum* ATCC13032 |
| ATCC13032_CK | Chromosomal insertion of the CK gene between NCgl0291 and NCgl0292 in *C. glutamicum* ATCC13032 |
| ATCC13032_DargR_CK | Chromosomal deletion of argR and chromosomal insertion of the CK gene between NCgl0291 and NCgl0292 in *C. glutamicum* ATCC13032 |

Example 5: Cloning of the Gene AGAT-Mp Coding for an L-Arginine: Glycine Amidinotransferase (AGAT, EC 2.1.4.1) Derived from *Moorena producens*

*Moorena producens* is a filamentous cyanobacterium. The genome of the *Moorena producens* strain PAL-Aug. 15, 2008-1 was published by Leao et al. (Leao T, Castelão G, Korobeynikov A, Monroe E A, Podell S, Glukhov E, Allen E E, Gerwick W H, Gerwick L, Proc Natl Acad Sci USA. 2017 Mar. 21; 114(12):3198-3203. doi: 10.1073/pnas.1618556114; Genbank accession Number CP017599.1). It contains an open reading frame coding for a L-arginine: glycine amidinotransferase (AGAT, EC 2.1.4.1; locus_tag BJP34_00300 shown in SEQ ID NO:8). SEQ ID NO:9 shows the derived amino acid sequence (Genbank accession Number WP_070390602).

Using the software tool "Optimizer" (http://genomes.urv.es/OPTIMIZER/) the amino acid sequence was translated back into a DNA sequence optimized for the codon usage of *C. glutamicum*. The 5'-end of the optimized gene was expanded with a BsaI restriction site, a 5'-UTR sequence for assembly cloning and a ribosomal binding site. At the 3'-end a second stop-codon, a sequence for assembly cloning and a BsaI-site was added. The resulting DNA sequence was named AGAT-Mp-insert (SEQ ID NO:10). It was ordered for gene synthesis from Eurofins Genomics GmbH (Ebersberg, Germany) and it was delivered as part of a cloning plasmid with an ampicillin resistance gene.

The cloning plasmid containing the AGAT-Mp-insert was digested using the restriction endonuclease BsaI and the DNA was purified with the "QIAquick PCR Purification Kit".

The *E. coli-C. glutamicum* shuttle plasmid pLIB_P consists of the replication origin from pBL1 (for *C. glutamicum*), the pSC101 replication origin (for *E. coli*) and a kanamycin resistance gene. Following a unique NotI restriction site it has a strong promoter, two inversely orientated BsaI-sites and the BioBricks Terminator BBa_B1006 (SEQ ID NO:11).

pLIB_P was digested using the restriction endonuclease BsaI and the DNA was purified with the "QIAquick PCR Purification Kit".

The DNA solutions of both BsaI digested plasmids were joined, and matching sequence ends were assembled using the "NEBuilder HiFi DNA Assembly Cloning Kit". The product was transformed into "NEB Stable Competent *E. coli* (High Efficiency)" and cells were grown on LB agar containing 25 mg/l kanamycin. A proper plasmid clone was identified by restriction digestion and DNA sequencing. The resulting plasmid was named pLIB_P_AGAT-Mp.

Example 6: Synthesis of the Gene AaDH-Mt Coding for an NADH Dependent AaDH Derived from *Mycobacterium tuberculosis* H37Ra The open reading frame MRA_2804 of *Mycobacterium tuberculosis* H37Ra presumably codes for an NADH dependent amino acid dehydrogenase (Genbank accession CP000611 locus_tag="MRA_2804", SEQ ID NO: 12). SEQ ID NO: 13 shows the derived amino acid sequence.

Using the software tool "Codon Optimization Tool" (Integrated DNA Technologies Inc., Coralville, Iowa, USA) the open reading frame was optimized for the codon usage of *C. glutamicum*. The resulting sequence was expanded with a 5'-UTR consisting of a BsaI restriction site, a homologous region for assembly cloning, the strong Pg3N3 promoter and a ribosomal binding site. Additionally, the 3'-end was expanded with a random spacer sequence, a homologous region for assembly cloning and a BsaI restriction site. The resulting DNA sequence was named AaDH-Mt-insert (SEQ ID NO: 14). It was ordered for gene synthesis from Invitrogen/Geneart (Thermo Fisher Scientific, Waltham, USA) and it was delivered as part of a cloning plasmid with an ampicillin resistance gene. The optimized gene was named AaDH-Mt.

Example 7: Synthesis of the Gene AtGGT1 Coding for a Glyoxylate Aminotransferase Derived from *Arabidopsis thaliana*

The gene GGT1 of *Arabidopsis thaliana* (Genbank accession Number NM_102180, SEQ ID NO: 15) codes for a glutamate:glyoxylate aminotransferase (Genbank accession Number NP_564192, SEQ ID NO: 16). The protein has been shown to catalyze the reactions glyoxylate+L-alanine=glycine+pyruvate (EC 2.6.1.44), 2-oxoglutarate+L-alanine=L-glutamate+pyruvate (EC 2.6.1.2), and 2-oxoglutarate+glycine=glyoxylate+L-glutamate (EC 2.6.1.4; Liepman A H, Olsen L J., Plant Physiol. 2003 January; 131(1):215-27. doi: 10.1104/pp. 011460).

Using the software tool "Codon Optimization Tool" (Integrated DNA Technologies Inc., Coralville, Iowa, USA) the amino acid sequence of the GGT1 protein was translated back into a DNA sequence optimized for the codon usage of *C. glutamicum*. The resulting sequence was expanded with a 5'-UTR consisting of a BsaI restriction site, a homologous region for assembly cloning and a ribosomal binding site. Additionally, the 3'-end was expanded with a homologous region for assembly cloning and a BsaI restriction site. The resulting DNA sequence was named AtGGT1-insert (SEQ ID NO:17). It was ordered for gene synthesis from Invitrogen/Geneart (Thermo Fisher Scientific, Waltham, USA) and it was delivered as part of a cloning plasmid with an ampicillin resistance gene. The optimized gene was named AtGGT1.

Example 8: Cloning of a Plasmid for the Co-Expression of AGAT-Mp and AaDH-Mt

For the combined expression of AGAT-Mp and AaDH-Mt, the synthetic gene AaDH-Mt was cloned into plasmid pLIB_P_AGAT-Mp.

The Plasmid pLIB_P_AGAT-Mp was digested using the restriction endonuclease NotI and the DNA was purified with the "QIAquick PCR Purification Kit". The plasmid containing the synthetic sequence AaDH-Mt-insert (SEQ ID NO:14) was digested using the restriction endonuclease BsaI and the resulting DNA was purified with the "QIAquick PCR Purification Kit".

A dummy DNA was designed having compatible ends for assembly cloning. It was named dummy-insert (SEQ ID NO:18) and it was ordered for gene synthesis from Invitrogen/Geneart (Thermo Fisher Scientific, Waltham, USA) as a linear double stranded DNA fragment.

The DNA of NotI digested pLIB_P_AGAT-Mp was joined with the BsaI digested plasmid containing AaDH-Mt-insert and the dummy-insert by using the "NEBuilder HiFi DNA Assembly Cloning Kit". The product was transformed into "NEB Stable Competent *E. coli* (High Efficiency)" (New England Biolabs, Ipswich, USA) and cells were grown on LB agar containing 25 mg/l kanamycin. A proper plasmid clone was identified by restriction digestion and DNA sequencing. The resulting plasmid was named pLIB_AaDH-Mt_AGAT-Mp.

Example 9: Cloning of a Plasmid for the Co-Expression of AGAT-Mp, AaDH-Mt and AtGGT1

For the combined expression of AGAT-Mp, AaDH-Mt and AtGGT1, the synthetic genes AaDH-Mt and AtGGT1 were cloned into plasmid pLIB_P_AGAT-Mp.

The Plasmid pLIB_P_AGAT-Mp was digested using the restriction endonuclease NotI and the DNA was purified with the "QIAquick PCR Purification Kit". The plasmid containing the synthetic sequence AaDH-Mt-insert (SEQ ID NO: 14) was digested using the restriction endonuclease BsaI and the resulting DNA was purified with the "QIAquick PCR Purification Kit". The plasmid containing the synthetic sequence AtGGT1-insert (SEQ ID NO: 17) was digested using the restriction endonuclease BsaI and the resulting DNA was purified with the "QIAquick PCR Purification Kit".

The DNA of NotI digested pLIB_P_AGAT-Mp was joined with the BsaI digested plasmid containing AaDH-Mt-insert and with the BsaI digested plasmid containing AtGGT1-insert using the "NEBuilder HiFi DNA Assembly Cloning Kit". The product was transformed into "NEB Stable Competent *E. coli* (High Efficiency)" and cells were grown on LB agar containing 25 mg/l kanamycin. A proper plasmid clone was identified by restriction digestion and DNA sequencing. The resulting plasmid was named pLIB_AaDH-Mt_AtGGT1_AGAT-Mp.

Example 10: Cloning of a Plasmid for the Co-Expression of AGAT-Mp and AtGGT1

For the combined expression of AGAT-Mp and AtGGT1, the gene AaDH-Mt was deleted from the plasmid pLIB_AaDH-Mt_AtGGT1_AGAT-Mp.

The Plasmid pLIB_AaDH-Mt_AtGGT1_AGAT-Mp was digested using the restriction endonucleases SacI and SalI and the DNA was purified with the "QIAquick PCR Purification Kit". The Ends of the linear DNA were blunted using the Fast DNA End Repair Kit (Thermo Fisher Scientific, Waltham, USA) and the DNA was purified. The DNA was subjected to self ligation using the Rapid Ligation Kit (Thermo Fisher Scientific, Waltham, USA). The ligated product was transformed into "NEB Stable Competent *E. coli* (High Efficiency)" and cells were grown on LB agar containing 25 mg/l kanamycin. A proper plasmid clone was identified by restriction digestion and the resulting plasmid was named pLIB_AtGGT1_AGAT-Mp.

Example 11: Transformation of *C. glutamicum* Strains with Various Plasmids

The following strains of *C. glutamicum* were transformed with the various plasmids by electroporation (Table 8). Plasmid containing cells were selected with 25 mg/l kanamycin.

- *C. glutamicum* ATCC13032: commonly used wild type strain (Kinoshita et al., J. Gen. Appl. Microbiol. 1957; 3(3):193-205)
- *C. glutamicum* ATCC13032_DargR: chromosomal deletion of argR in *C. glutamicum* ATCC13032
- *C. glutamicum* ATCC13032_CK: chromosomal insertion of the CK gene between NCgl0291 and NCgl0292 in *C. glutamicum* ATCC13032
- *C. glutamicum* ATCC13032_DargR_CK: Chromosomal deletion of argR and chromosomal insertion of the CK gene between NCgl0291 and NCgl0292 in *C. glutamicum* ATCC13032

TABLE 8

List of plasmid-containing *C. glutamicum* strains

| Plasmid | Recipient strain | Resulting strain |
| --- | --- | --- |
| pLIB_P | ATCC13032 | ATCC13032/pLIB_P |
| pLIB_P_AGAT-Mp | ATCC13032 | ATCC13032/pLIB_P_AGAT-Mp |
| pLIB_AaDH-Mt_AtGGT1_AGAT-Mp | ATCC13032 | ATCC13032/pLIB_AaDH-Mt_AtGGT1_AGAT-Mp |
| pLIB_AaDH-Mt_AtGGT1_AGAT-Mp | ATCC13032_DargR | ATCC13032_DargR/pLIB_AaDH-Mt_AtGGT1_AGAT-Mp |
| pLIB_P_AGAT-Mp | ATCC13032_CK | ATCC13032_CK/pLIB_P_AGAT-Mp |
| pLIB_AaDH-Mt_AGAT-Mp | ATCC13032_CK | ATCC13032_CK/pLIB_AaDH-Mt_AGAT-Mp |
| pLIB_AtGGT1_AGAT-Mp | ATCC13032_CK | ATCC13032_CK/pLIB_AtGGT1_AGAT-Mp |
| pLIB_AaDH-Mt_AtGGT1_AGAT-Mp | ATCC13032_CK | ATCC13032_CK/pLIB_AaDH-Mt_AtGGT1_AGAT-Mp |
| pLIB_AaDH-Mt_AtGGT1_AGAT-Mp | ATCC13032_DargR_CK | ATCC13032_DargR_CK/pLIB_AaDH-Mt_AtGGT1_AGAT-Mp |

Example 12: Impact of the L-Arginine: Glycine Amidinotransferase Gene on GAA Production To assess the impact of the L-arginine: glycine amidinotransferase gene (AGAT-Mp) on GAA production, strains ATCC13032/pLIB_P and ATCC13032/pLIB_P_AGAT-Mp were cultivated in the Wouter Duetz system in production medium and the resulting GAA titers were determined as described above.

TABLE 9

Impact of the expression of the L-arginine:glycine amidinotransferase gene on GAA production

| Strain | GAA |
| --- | --- |
| ATCC13032/pLIB_P | not detectable |
| ATCC13032/pLIB_P_AGAT-Mp | 120 mg/l |

The cultivation of the strain having the L-arginine: glycine amidinotransferase gene resulted in GAA production, compared to the strain lacking L-arginine: glycine amidinotransferase gene (see Table 9). We conclude that the presence of the heterologous L-arginine: glycine amidinotransferase gene enables the production of GAA.

Example 13: Impact of the Carbamate Kinase Gene on GAA Production

To assess the impact of the carbamate kinase gene on GAA production, strains ATCC13032/pLIB_P_AGAT-Mp and ATCC13032_CK/pLIB_P_AGAT-Mp were cultivated in the Wouter Duetz system in production medium and the resulting GAA titers were determined as described above.

TABLE 10

Impact of the expression of the carbamate kinase gene on GAA production

| Strain | GAA |
|---|---|
| ATCC13032/pLIB_P_AGAT-Mp | 120 mg/l |
| ATCC13032_CK/pLIB_P_AGAT-Mp | 223 mg/l |

The cultivation of the strain having the carbamate kinase gene resulted in a higher GAA titre, compared to the strain lacking a carbamate kinase gene (see Table 10). We conclude that the presence of the carbamate kinase gene improves the production of GAA.

Example 14: Impact of the Combined Presence of the Carbamate Kinase Gene and the Glyoxylate Aminotransferase Gene on GAA Production To assess the impact of the combined presence of the carbamate kinase gene (CK) and the glyoxylate aminotransferase gene (AtGGT1) on GAA production, strains ATCC-13032_CK/pLIB_P_AGAT-Mp and ATCC13032_CK/pLIB_AtGGT1_AGAT-Mp were cultivated in the Wouter Duetz system in production medium and the resulting GAA titers were determined as described above.

TABLE 11

Impact of the combined presence of the carbamate kinase gene and the glyoxylate aminotransferase gene on GAA production

| Strain | GAA |
|---|---|
| ATCC13032_CK/pLIB_P_AGAT-Mp | 223 mg/l |
| ATCC13032_CK/pLIB_AtGGT1_AGAT-Mp | 337 mg/l |

The cultivation of the strain having the carbamate kinase gene and the glyoxylate aminotransferase gene resulted in a higher GAA titre, compared to the strain lacking the glyoxylate aminotransferase gene (see Table 11). We conclude that the combined presence of the carbamate kinase gene and the glyoxylate aminotransferase gene improves the production of GAA.

Example 15: Impact of the Combined Presence of the Carbamate Kinase Gene and the NADH-Dependent Amino Acid Dehydrogenase Gene on GAA Production To assess the impact of the combined presence of the carbamate kinase gene (CK) and the NADH-dependent amino acid dehydrogenase gene (AaDH-Mt) on GAA production, strains ATCC13032_CK/pLIB_P_AGAT-Mp and ATCC13032_CK/pLIB_AaDH-Mt_AGAT-Mp were cultivated in the Wouter Duetz system in production medium and the resulting GAA titers were determined as described above.

TABLE 12

Impact of the combined presence of the carbamate kinase gene and the NADH-dependent amino acid dehydrogenase gene on GAA production

| Strain | GAA |
|---|---|
| ATCC13032_CK/pLIB_P_AGAT-Mp | 223 mg/l |
| ATCC13032_CK/pLIB_AaDH-Mt_AGAT-Mp | 545 mg/l |

The cultivation of the strain having the carbamate kinase gene and the NADH-dependent amino acid dehydrogenase gene resulted in a higher GAA titer, compared to the strain lacking the NADH-dependent amino acid dehydrogenase gene (see Table 12). We conclude that the combined presence of the carbamate kinase gene and the NADH-dependent amino acid dehydrogenase gene improves the production of GAA.

Example 16: Impact of the Combined Presence of the Carbamate Kinase Gene, the NADH-Dependent Amino Acid Dehydrogenase Gene and the Glyoxylate Aminotransferase Gene on GAA Production To assess the impact of the combined presence of the carbamate kinase gene (CK), the glyoxylate aminotransferase gene (AtGGT1) and the NADH-dependent amino acid dehydrogenase gene (AaDH-Mt) on GAA production, strains ATCC13032_CK/pLIB_AtGGT1_AGAT-Mp, ATCC13032_CK/pLIB_AaDH-Mt_AGAT-Mp and ATCC-13032_CK/pLIB_AaDH-Mt_AtGGT1_AGAT-Mp were cultivated in the Wouter Duetz system in production medium and the resulting GAA titers were determined as described above.

TABLE 13

Impact of the combined presence of the carbamate kinase gene, the NADH-dependent amino acid dehydrogenase gene and the glyoxylate aminotransferase gene on GAA production

| Strain | GAA |
|---|---|
| ATCC13032_CK/pLIB_AtGGT1_AGAT-Mp | 337 mg/l |
| ATCC13032_CK/pLIB_AaDH-Mt_AGAT-Mp | 545 mg/l |
| ATCC13032_CK/pLIB_AaDH-Mt_AtGGT1_AGAT-Mp | 657 mg/l |

The cultivation of the strain having a combination of the carbamate kinase gene, the NADH-dependent amino acid dehydrogenase gene and the glyoxylate aminotransferase gene resulted in a higher GAA titre, compared to the strains lacking either the NADH-dependent amino acid dehydrogenase gene or the glyoxylate aminotransferase gene (see Table 13). We conclude that the combined presence of the carbamate kinase gene, the NADH-dependent amino acid dehydrogenase gene and the glyoxylate aminotransferase gene improves the production of GAA.

Example 17: Impact of the Deletion of the argR Gene in Combination with the Presence of the Carbamate Kinase Gene, the NADH-Dependent Amino Acid Dehydrogenase Gene and the Glyoxylate Aminotransferase Gene on GAA Production To assess the impact of the deletion of the argR gene (DargR) in combination with the presence of the carbamate kinase gene (CK), the glyoxylate aminotransferase gene (AtGGT1) and the NADH-dependent amino acid dehydrogenase gene (AaDH-Mt) on GAA production, strains ATCC13032/pLIB_AaDH-Mt_AtGGT1_AGAT-Mp, ATCC13032_DargR/pLIB_AaDH-Mt_AtGGT1_AGAT-Mp and ATCC13032_DargR_CK/pLIB_AaDH-Mt_AtGGT1_AGAT-Mp were cultivated in the Wouter Duetz system in production medium and the resulting GAA titers were determined as described above.

TABLE 14

Impact of the deletion of the argR gene in combination with the presence of the carbamate kinase gene, the NADH-dependent amino acid dehydrogenase gene and the glyoxylate aminotransferase gene on GAA production

| Strain | GAA |
|---|---|
| ATCC13032/pLIB_AaDH-Mt_AtGGT1_AGAT-Mp | 377 mg/l |
| ATCC13032_DargR/pLIB_AaDH-Mt_AtGGT1_AGAT-Mp | 589 mg/l |
| ATCC13032_DargR_CK/pLIB_AaDH-Mt_AtGGT1_AGAT-Mp | 845 mg/l |

The cultivation of the strain having a deleted argR gene in combination with the presence of the glyoxylate aminotransferase gene and the NADH-dependent amino acid dehydrogenase gene resulted in a higher GAA titer, compared to the strain with a wildtype argR gene (see Table 14). The cultivation of the strain having a deleted argR gene in combination with the presence of the carbamate kinase gene, the glyoxylate aminotransferase gene and the NADH-dependent amino acid dehydrogenase gene resulted in a higher GAA titer, compared to both strains lacking the carbamate kinase gene (see Table 14).

We conclude that the deletion of the argR gene in combination with the presence of the carbamate kinase gene, the glyoxylate aminotransferase gene and the NADH-dependent amino acid dehydrogenase gene improves the production of GAA.

The invention claimed is:

1. A microorganism, comprising:
   at least one heterologous gene coding for a protein having a function of a L-arginine:glycine amidinotransferase belonging to E.C. 2.1.4.1;
   at least one heterologous gene coding for a protein having a function of a carbamate kinase belonging to E.C. 2.7.2.2; and
   further comprising at least one gene coding for a protein having a function of a NADH-dependent amino acid dehydrogenase belonging to E.C. 1.4.1.

2. The microorganism of claim 1, wherein an activity of the at least one protein having the function of a carbamate kinase is increased compared to the wildtype microorganism.

3. The microorganism of claim 1, comprising at least one heterologous gene coding for a protein having the function of a carbamate kinase.

4. The microorganism of claim 1, wherein an activity of the protein having the function of a NADH-dependent amino acid dehydrogenase is increased compared to the wildtype microorganism.

5. The microorganism of claim 1, wherein the protein having the function of a NADH-dependent amino acid dehydrogenase is a heterologous protein.

6. The microorganism of claim 1, further comprising at least one gene coding for a protein having the function of a glyoxylate aminotransferase.

7. The microorganism of claim 1, wherein the microorganism has an increased ability to produce L-arginine from L-ornithine compared to the wildtype microorganism.

8. The microorganism of claim 7, wherein an expression of an argR gene is attenuated compared to the wildtype microorganism, wherein said argR gene codes for an arginine responsive repressor protein ArgR.

9. The microorganism of claim 1, wherein the microorganism belongs to a genus *Corynebacterium*, to a genus *Bacillus*, to a genus Enterobacteriaceae or to a genus *Pseudomonas*.

10. A method for a fermentative production of guanidino acetic acid (GAA), the method comprising:
   a) cultivating the microorganism as defined in claim 1 in a medium, and
   b) accumulating GAA in the medium to form a GAA containing fermentation broth.

11. The method of claim 10, further comprising isolating GAA from the GAA containing fermentation broth.

12. The microorganism as claimed in claim 1, further comprising a gene coding for an enzyme having an activity of a guanidinoacetate N-methyltransferase.

13. The microorganism of claim 12, wherein the gene coding for an enzyme having the activity of a guanidinoacetate N-methyltransferase is overexpressed.

14. A method for the fermentative production of creatine, the method comprising:
   a) cultivating the microorganism according to claim 1 in a medium, and
   b) accumulating creatine in the medium to form a creatine containing fermentation broth.

15. The method of claim 14, further comprising isolating creatine from the creatine containing fermentation broth.

* * * * *

```
                          SEQUENCE LISTING

Sequence total quantity: 24
SEQ ID NO: 1              moltype = DNA  length = 44
FEATURE                   Location/Qualifiers
source                    1..44
                          mol_type = other DNA
                          organism = synthetic construct
SEQUENCE: 1
tcgagctcgg tacccgggga tcctctggct gatgatgatc tcac            44

SEQ ID NO: 2              moltype = DNA  length = 45
FEATURE                   Location/Qualifiers
source                    1..45
                          mol_type = other DNA
                          organism = synthetic construct
SEQUENCE: 2
ctagggatag tagacacttc acaagtgtct tacctcggct ggttg           45

SEQ ID NO: 3              moltype = DNA  length = 47
FEATURE                   Location/Qualifiers
source                    1..47
                          mol_type = other DNA
                          organism = synthetic construct
SEQUENCE: 3
cttgtgaagt gtctactatc cctagaatta ctcagcgggc gcaccac         47

SEQ ID NO: 4              moltype = DNA  length = 46
FEATURE                   Location/Qualifiers
source                    1..46
                          mol_type = other DNA
                          organism = synthetic construct
SEQUENCE: 4
agcttgcatg cctgcaggtc gactctgcac gacggttcag ctcttc          46

SEQ ID NO: 5              moltype = DNA  length = 933
FEATURE                   Location/Qualifiers
source                    1..933
                          mol_type = genomic DNA
                          organism = Enterococcus faecalis
                          strain = Enterococcus faecalis ATCC 29212
SEQUENCE: 5
atggggaaaa aaatggtcgt tgcactaggc ggaaatgcca tcctttcaaa tgatgctagc   60
gcacacgcac aacagcaagc attagttcaa acatctgcct atttagttca tttaattaaa  120
caagggcatc ggttgattgt ttcacatggc aatggtccac aagtcggaaa tctattattg  180
caacaacaag cagctgattc tgaaaaaaat ccagcgatgc cgctagatac gtgtgttgct  240
atgacacaag gaagtatcgg ctactggttg tccaatgcgc ttaatcaaga attaaacaaa  300
gcaggaatca agaaacaagt ggctactgtt ttaacacagg tggtcgtaga tccagcagat  360
gaggcattca aaaatccaac aaaaccgatc ggtccatttt taacagaagc tgaagccaaa  420
gaagcaatgc aagcaggtgc tatttttaaa gaagatgcag gacgtggctg gcgcaaagtc  480
gttccaagtc ctaagccaat tgacatccac gaggctgaga ctattaatac cttaataaaa  540
aatgatataa ttaccatttc atgtggtggt ggtggcatcc ctgtcgtagg acaagaatta  600
aaaggtgtcg aagcagtaat cgataaagat tttgcttctg aaaaactggc agaattagtg  660
gatgcggatg cactagttat tttaactggc gtggattatg tgtgtattaa ttatggcaaa  720
ccagatgaaa acaattaaac caatgtcact gtagcagagt tggaagaata caaacaagcg  780
ggtcattttg caccaggtag tatgttaccg aaaattgaag ccgccattca gtttgtagaa  840
agccaaccca ataaacaagc aattatcact tctttgaaa acttaggaag tatgagcggc  900
gatgaaatcg taggaacggt tgtgacaaaa taa                              933

SEQ ID NO: 6              moltype = AA  length = 310
FEATURE                   Location/Qualifiers
```

```
source                  1..310
                        mol_type = protein
                        note = strain: Enterococcus faecalis ATCC 29212
                        organism = Enterococcus faecalis
SEQUENCE: 6
MGKKMVVALG GNAILSNDAS AHAQQQALVQ TSAYLVHLIK QGHRLIVSHG NGPQVGNLLL     60
QQQAADSEKN PAMPLDTCVA MTQGSIGYWL SNALNQELNK AGIKKQVATV LTQVVVDPAD    120
EAFKNPTKPI GPFLTEAEAK EAMQAGAIFK EDAGRGWRKV VPSPKPIDIH EAETINTLIK    180
NDIITISCGG GGIPVVGQEL KGVEAVIDKD FASEKLAELV DADALVILTG VDYVCINYGK    240
PDEKQLTNVT VAELEEYKQA GHFAPGSMLP KIEAAIQFVE SQPNKQAIIT SLENLGSMSG    300
DEIVGTVVTK                                                           310

SEQ ID NO: 7            moltype = DNA  length = 3842
FEATURE                 Location/Qualifiers
source                  1..3842
                        mol_type = other DNA
                        organism = synthetic construct
SEQUENCE: 7
caactcggtc tcgacatgat tacgaattcg agctcggtac ccgcacaatc gcgtcgattg     60
aacgctcccc cggcatcatt gcccctagacg gaccgttcac ccacgatcac gtctccgtac   120
gtggcattcg cctccattta gcagaggcag gctcccccac caaaccctg gttcttctga    180
tccacgggc tttcggcggt tggtacgact accgcgaagt catcggccca ctcgcagatg    240
ccggcttcca cgtcgccgcc atcgatctac gcggctacga catgtccgac aaaccccaa    300
caggctacga cctccgccac gcagccgag aactcagcag cgttatcgca gctctcggcc    360
acgatgacgc acttcttgtc ggctccgaca ccggcgccag catcgcctgg gctatcgctt    420
ccatgtaccc cgaacgggtc cgcggcctaa ttcccctcgc cgcgatccat ccccttgaca    480
tgcgacgcgc catccgacga aaaccccacc tacacgtctc tgacctcagc cgacttgctc    540
cttttcggtt gccctcattc ctgcataacc tcttccactt cggaatcacc agcgaagctc    600
gacgtgagat cgtcaacaac acgtcctcgt cctaccagcg cagcaacgca ttcacagaga    660
cagtgctcct ccgcaaaaaa gcactatcga tcgaccaac catcacccc atcatccgca    720
ccaaccgcta cctcgttggg tcgatccccca gcaaacagt ctccgcaccg gtgtggctgc    780
tcagaaccaa cactcgacgc tgggaacatc tagccaatac tgccgcgcact cgaacgacag    840
ggccattcac caccatcgcg atcccggcc gctacgaact cccctacctc gagaacctt     900
ccgaattgc agcaaccatc gcagagttc cgcgcaccac gttttaagca ctgtggctga     960
ggcgctgctg ctcatttggc gtcagaaggt cgcatgattt ggcgtgaat tagtggttt     1020
tccctggttt taccccggcg cattgaccgg accagacagg cgtgacaaga atcaagattt    1080
tcgccaggtt ttgtcacgtg tgtctggttt gagcgactcg aaaccaaaca ggcgtgccaa    1140
aacttagatg ttttagcaat ttttgtcacg tgtgtctggt ttcatctagt tcgaccgcaa    1200
accctcacgga tttcccccta gtcactcaaa aaccaaaact ccctatatgc ccctctaagc    1260
gcttgggatt ccccgatttc cttttaggtg gaatgtaaaa agaaacccc ctgaaattca    1320
atgaagaatt tcaggggggtt tccgctatcg gctagctaag tgaattactt ggttacaacg    1380
gttcccacga tttcgtcgcc ggacatggag ccgaggtttt ccaggaggt gatgatggcc    1440
tgtttgtttg gctgggactc cacgaactgg atagccgctt cgatcttgg ccatgctgg    1500
cctggtgcga agtggccagc ctgcttgtac tcctcgagtt ctgccacggt aacgttggtg    1560
agttgcttct cgtcaggctt gccgtagttg atgcacacat aatcaacgcc ggtcaggatc    1620
acgagtgcgt ctgcgtcaac tagctctgcg agcttttcgg aagcaaagtc cttatcaatc    1680
acggcttcca cgccctgag ttcttggcca acgactggaa taccgccacc gccgcatgca    1740
atagtgatga tgtcgttctt gatcaggggtg ttaatagtct ctgcttcgtg gatgtcgata    1800
ggctttggag acgggacaac cttacgccag ccgcggcctg cgtcctcctt gaagattgcg    1860
cccgcctgca ttgcctcttt tgcctctgct tcagtgagga atgggccgat tggcttggtt    1920
gggttcttga acgcttcatc ggctgggtca acgacacacgg gggtcagaac ggttgcgac    1980
tgcttttga taccagcctt gttaagttct tggttgagag cgttggacag ccagtatccg    2040
atggatccct gggtcatagc aacgcaggtg tccagtggca ttgccgggtt cttttcgctg    2100
tctgctgctt gctgttggag cagcaggttt ccaacctgtg ggccgttgcc gtgggatacg    2160
atcagacggt gaccctgctt gatgaggtga accaggtatg cggaggtctg gaccagtgct    2220
tgctgctgtg cgtgtgcgga tcgtcgttg ataggattc gttaccgcc cagcgcgacc    2280
accatttct tgcccatggg taaaaaatcc tttcgtaggt ttccgcaccg agcatataca    2340
tcttttgaaa atccgtcaga tggcgcttcg caaaagtact tggtgcgaca cctcccaatg    2400
ataggcctt ttgttgatat tgcaacgaaa tttttcgacg gacctattta tcgggtagcg    2460
ggtcacaagc ccggaataat tggcagctaa gtagggttga agggcataag gcttcctcaa    2520
ttttcgaaag gaacattcct gttatggtac ccgaaaaaa aaaccccgcc ctgtcagggg    2580
cggggttttt ttttcccata ccaatagaca cctctcctat tccaggccct taaaacgcca    2640
cacaggattg gtcgtatcta tctcggattg gcgattcac tgccaagacc aaaccacact    2700
gcccacgcaa cggaaaaaacc gcaatgtgg gcatctgtga ccggttccga gcccccaaa    2760
ccaaaccaca ctgcccacgc aacgaaaaa ccgcaatcgt gggcatccct gtctggtcct    2820
agctcccgac gactaagaaa ccgcgcactg catcgtatcg acaggctgag tcagcgcggt    2880
gatgtcgccg atccgctcct gtacctcttc ggcagtgaga acgtaaccgg tatcggagcc    2940
gtcgatcgct gcgccgaaga caacaccaac cacttcaccc atttcgttgg tcattgggcc    3000
gccggagttt ccagattgga tccgcgcg gactgaatag gcttcgcgtt cgtgctgcg    3060
gttggcgtaa atgttgctgc cggtgatcat gatgcgttcg cggacccctgg ctggggaggc    3120
gttgaaaggt ccggactgtg gaatcccat gacgattgct tcatcgccag tgtctagcgg    3180
agtggatgcc cacggcagtg gatccaagcc gaggtcaggg ctgaaagga ctgcgatgtc    3240
caggttcggg tcgtagaaca ctacctctgc ggagcgggtt ccgatcatgg tatccaggct    3300
gaccgtgag gtacctgcaa caacgtgggc gttggtcaca acgtagtcgg gggatgccac    3360
aaagccagaa cccatgagtc ggcggctgca ttcttgggcg tcacccatca cgtggatgac    3420
ggacgggcgc attgcttcga ctaggtcaac gttggtgacg ttgatttcgg gggcgtccac    3480
ttccaccgag gatccgccgg tgaaggggga aatcagtggt ggggaggccgg attcgctgag    3540
catcgcagcg attttggagg gcagggtatc taggccttgc ggggtgtatt tgtctacaaa    3600
gcccaggatg cgggagtctc taattccgct ggcgacagtt ccggggaggc ctgtggccag    3660
```

-continued

```
gggaattgcg acgagccaca ccacgatcaa ggtggccaat acttggaaaa tggcgccgag   3720
cccagaatct aaggtcctgg aacttccgaa tttgatgttg tctctaatcg cagcacccaa   3780
gtgggcgccg atgagatttc ggggatcctc tagagtcgac ctgcaggcat gagacccatt   3840
ga                                                                  3842

SEQ ID NO: 8            moltype = DNA   length = 1146
FEATURE                 Location/Qualifiers
source                  1..1146
                        mol_type = genomic DNA
                        organism = Moorena producens
                        strain = Moorena producens PAL-8-15-08-1
SEQUENCE: 8
atgtcggaaa aaattgttaa ttcctggaat gaatgggatg aattggaaga aatggtggta    60
ggaattgcag actatgctag ctttgaacca aaagaaccag ggaatcatcc gaaattaaga   120
aatcaaaatt tagcggaaat cattcctttc cccagtggac ctaaagaccc taagtccttt   180
gaaaaagcta atgaagaatt aaatggactg gcttatttat aaaagacca cgatgtgata   240
gtaagaagac ccgaaaaaat tgattttact aaatctctaa aaacaccta ctttgaagtt   300
gcaaatcaat actgtggagt ctgtcctcgg gatgtcatga ttaccttgg gaatgaaatc   360
atggaagcga ctatgtcgaa gagagctaga tttttgaat acttaccta ccggaaattg   420
gtctatgaat attggaataa agacgagcat atgatttgga atgctgcgcc taaaccgact   480
atgcaggata gtatgtatct agagaatttc tgggagctgt ctttagaaga acgatttaag   540
cgtatgcatg attttgaatt ttgtattaca caagatgaag taattttga tgcggctgac   600
tgtagcagat taggaaagga tatattagtt caggaatcga tgacaacaaa tagaacagga   660
attcggtggt taaaaaagca cctagaacca gagggatttc gggttcaccc tgttcatttt   720
cccctttgatt tttttccctc acacattgac tgtacgtttg ttcctttgcg accaggtctt   780
attttgacaa accctgaaag acctatacgg gaagaggagg agaagatttt taaagagaat   840
ggctgggagt tgatcacagt tcctcaaccg acttgctcga atgatgaaat gccaatgttt   900
tgccagtcca gtaagtggtt gtcaatgaat gttctgagta taccaccgac aaaggttatc   960
tgtgaggaaa gagaaaaacc tctccaagaa ttgttggata gcatggatt tgaggttttt   1020
cctttacct ttagacatgt ctttgaattt gggggtctt tcattgtgc aacttgggat   1080
attcgccgaa aaggtgagtg tgaagattat ttaccaaatt taaactatca accgatttgt   1140
ggttaa                                                             1146

SEQ ID NO: 9            moltype = AA   length = 381
FEATURE                 Location/Qualifiers
source                  1..381
                        mol_type = protein
                        note = strain: Moorena producens PAL-8-15-08-1
                        organism = Moorena producens
SEQUENCE: 9
MSEKIVNSWN EWDELEEMVV GIADYASFEP KEPGNHPKLR NQNLAEIIPF PSGPKDPKVL    60
EKANEELNGL AYLLKDHDVI VRRPEKIDFT KSLKTPYFEV ANQYCGVCPR DVMITFGNEI   120
MEATMSKRAR FFEYLPYRKL VYEYWNKDEH MIWNAAPKPT MQDSMYLENF WELSLEERFK   180
RMHDFEFCIT QDEVIFDAAD CSRLGKDILV QESMTTNRTG IRWLKKHLEP RGFRVHPVHF   240
PLDFFPSHID CTFVPLRPGL ILTNPERPIR EEEEKIFKEN GWELITVPQP TCSNDEMPMF   300
CQSSKWLSMN VLSISPTKVI CEERERPLQE LLDKHGFEVF PLPFRHVFEF GGSFHCATWD   360
IRRKGECEDY LPNLNYQPIC G                                            381

SEQ ID NO: 10           moltype = DNA   length = 1362
FEATURE                 Location/Qualifiers
source                  1..1362
                        mol_type = other DNA
                        organism = synthetic construct
SEQUENCE: 10
ggtctccatc cgcgtcggag acgaagtaat tgacggcagc acctcgggca aactcgagcg    60
tctgcgggca agcttcgcat aaagacacga cgaattagac aacattagta atgctggaag   120
aaacaaccga gagcaggaag aacatgtcag aaaagattgt taactcctgg aacgaatggg   180
acgaacttga agaaatggtg gttggcatcg cggactacgc ttccttcgag ccaaaagaac   240
caggtaacca ccctaagcta cgcaaccaga acctggccga gatcatccca ttcccatccg   300
gcccaaagga cccaaaggtt ctcgaaaaag caaacgaaga gctgaacggc ctcgcatacc   360
tcctaaagga ccacgatgtt atcgtccgcc gcccagaaaa aattgatttc actaagtccc   420
ttaaaacccc atactcgag gtcgctaacc agtactgcgg cgtttgccca cgcgacgtta   480
tgattacctt cggtaatgag attatggagg ctaccatgag caagcgtgca cgcttcttcg   540
agtacttgcc ataccgtaag ctcgtctacg agtactggaa caaggatgaa catatgattt   600
ggaacgctgc tccaaagcct acgatgcagg actccatgta cttggagaac ttctgggagc   660
tgtccctcga ggagcgcttc aagcgcatgc acgacttcga attttgcatt acccaggacg   720
aggttatctt cgacgcagct gactgctccc gcctgggcaa ggacatcctg gtccaggagt   780
ccatgaccac caaccgcacc ggcattcgtt ggttgaagaa gcacctcgaa cctcgcggtt   840
tccgcgttca cccagtccac ttccctctcg acttcttccc ttctcacatt gactgcactt   900
tcgtccctct ccgtcccggc ctcatcctta ccaaccagag cgcccaatcc cgcgaagaag   960
aagaaaagat cttcaaggag aacggctggg agcttatcac cgtcccacaa cctacctgct  1020
ccaacgacga aatgcctatg ttctgccagt cctcgaagtg gctcagcatg aacgtccttt  1080
ctatctcccc aacaaaggtt attgcgaag agcgtgaaaa gccactacag gaactcctgg  1140
acaagcacgg cttcgaagtc tttccacctcc cattcgcgca cgttttgaa ttcggcgcgt  1200
cctttcactg cgccacttgg gacatcgcc gcaagggca atgcgaagac taactcccaa  1260
acctgaacta ccagcctatc tgcggctaat aagtccggta cccggggatc cgactcgcg  1320
ttaacttaag gtaccgaatt ctaagcttca caaaagaga cc                      1362

SEQ ID NO: 11           moltype = DNA   length = 7061
```

| FEATURE | Location/Qualifiers |
|---|---|
| source | 1..7061 |
| | mol_type = other DNA |
| | organism = synthetic construct |

SEQUENCE: 11

```
gacagtaaga cgggtaagcc tgttgatgat accgctgcct tactgggtgc attagccagt    60
ctgaatgacc tgtcacggga taatccgaag tggtcagact ggaaaatcag agggcaggaa   120
ctgcagaaca gcaaaaagtc agatagcacc acatagcaga cccgccataa aacgccctga   180
gaagcccgtg acgggctttt cttgtattat gggtagtttc cttgcatgaa tccataaaag   240
gcgcctgtag tgccatttac ccccattcac tgccagagcc gtgagcgcag cgaactgaat   300
gtcacgaaaa agacagcgac tcaggtgcct gatggtcgga gacaaaagga atattcagcg   360
atttgcccga gcttgcgagg gtgctactta agcctttagg gttttaaggt ctgttttgta   420
gaggagcaaa cagcgtttgc gacatccttt tgtaatactg cggaactgac taaagtagtg   480
agttatacac agggctggga tctattcttt ttatctttc ttattctttc tttattctat   540
aaattataac cacttgaata taaacaaaaa aaacacacaa aggtctagcg gaatttacag   600
agggtctagc agaatttaca agttttccag caaaggtcta gcagaattta cagataccca   660
caactcaaag gaaaaggact agtaattatc attgactagc ccatctcaat tggtatagtg   720
attaaaatca cctagaccaa ttgagatgta tgtctgaatt agttgttttc aaagcaaatg   780
aactagcgat tagtcgctat gacttaacgg agcatgaaac caagctaatt ttatgctgtg   840
tggcactact caaccccacg attgaaaacc ctacaaggaa agaacggacg gtatcgttca   900
cttataacca atacgctcag atgatgaaca tcagtaggga aaatgcttat ggtgtattag   960
ctaaagcaac cagagagctg atgacgagaa ctgtggaaat caggaatcct ttggttaaag  1020
gctttgagat tttccagtgg acaaactatg ccaagttctc aagcgaaaaa ttagaattag  1080
tttttagtga agagatattg ccttatcttt tccagttaaa aaaattcata aaatataatc  1140
tggaacatgt taagtctttt gaaaacaaat actctatgag gatttatgag tggttattaa  1200
aagaactaac acaaaagaaa actcacaagg caaatataga gattagcctt gatgaattta  1260
agttcatgtt aatgcttgaa aataactacc atgagtttaa aaggcttaac caatgggttt  1320
tgaaaccaat aagtaaagat ttaaacactt acagcaatat gaaattggtg gttgataagc  1380
gaggccgccc gactgatacg ttgattttcc aagttgaact agatagacaa atggatctcg  1440
taaccgaact tgagaacaac cagataaaaa tgaatggtga caaaatacca acaaccatta  1500
catcagattc ctacctacat aacggactaa gaaaaacact acacgatgct ttaactgcaa  1560
aaattcagct caccagtttt gaggcaaaat tttgagtga catgcaaagt aagcatgatc  1620
tcaatggttc gttctcatgg ctcacgcaaa acaacgaaac cacactagag aacatactgg  1680
ctaaatacgg aaggatctga ggttcttatg gctcttgtat ctatcagtga agcatcaaga  1740
ctaacaaaca aaagtagaac aactgttcac cgttacatat caaagggaaa actgtccata  1800
tgcacagatg aaaacggtgt aaaaaagata gatacatcag agcttttacg agttttttggt  1860
gcattcaaag ctgttcacca tgaacagatc gacaatgtaa cagatgaaca gcatgtaaca  1920
cctaatagaa caggtgaaac cagtaaaaca aagcaactag aacatgaaat tgaacacctg  1980
agacaacttg ttacagctca acagtcacac atagacagcc tgaaacaggc gatgctgctt  2040
atcgaatcaa agctgccgac aacacggag ccagtgacgc ctcccgtggg gaaaaaatca  2100
tggcaattct ggaagaaata gcgccattcg ccattcaggc tgcctgcagg gaaagccacg  2160
ttgtgtctca aaatctctga tgttacattg cacaagataa aaatatatca tcatgaacaa  2220
taaaactgtc tgcttacata aacagtaata caaggggtgt tatgagccat attcaacggg  2280
aaacgtcttg ctcgaggccg cgattaaatt ccaacatgga tgctgattta tatgggtata  2340
aatgggctcg cgataatgtc gggcaatcag gtgcgacaat ctatcgattg tatgggaagc  2400
ccgatgcgcc agagttgttt ctgaaacatg gcaaaggtag cgttgccaat gatgttacag  2460
atgagatggt cagactaaac tggctgacgg aatttatgcc tcttccgacc atcaagcatt  2520
ttatccgtac tcctgatgat gcatggttac tcaccactgc gatccccggg aaaacagcat  2580
tccaggtatt agaagaatat cctgattcag gtgaaaatat tgttgatgcg ctggcagtgt  2640
tcctgcgccg gttgcattcg attcctgttt gtaattgtcc ttttaacagc gatcgcgtat  2700
ttcgtctcgc tcaggcgcaa tcacgaatga ataacggttt ggttgatgcg agtgattttg  2760
atgacgagcg taatggctgg cctgttgaac aagtctggaa agaaatgcat aagcttttgc  2820
cattctcacc ggattcagtc gtcactcatg gtgatttctc acttgataac cttattttg  2880
acgaggggaa attaataggt tgtattgatg ttggacgagt cggaatcgca gaccgatacc  2940
aggatcttgc catcctatgg aactgcctcg gtgagttttc tccttcatta cagaaacggc  3000
tttttcaaaa atatggtatt gataatcctg atatgaataa attgcagttt catttgatgc  3060
tcgatgagtt tttctaatca gaattggtta attggttgta acactggcag agcattacgc  3120
tgacttgacg gacgcggc tttgttgaat aaatcgaact tttgctgagt tgaaggatca  3180
gatcacgcat cttcccgaca acgcagaccg ttccgtggca aagcaaaagt tcaaaatcac  3240
caactggtcc acctacaaca aagctctcat caaccgtggc tccctcactt tctggctgga  3300
tgatgggcct gcaggcctca gcgcgattca ggcctggtat gagtcagcaa caccttcttc  3360
acgaggcaga tctcagcgcc cccccccccc tagcttgtct acgtctgatg ctttgaatcg  3420
gacggacttg ccgatcttgt atgcggtgat ttttccctcg tttgcccact ttttaatggt  3480
ggcggggtg agagctacgc gggcggcgac ctgctgcgct ggtgatccaat attcggtgtc  3540
gttcactggt tccccttct gatttctggc atagaagaac cccgtgaac tgtgtgggtc  3600
cgggggttgc tgattttgc gagacttctc gcgcaattcc ctagcttagg tgaaaacacc  3660
atgaaacact agggaaacac ccatgaaaca cccattaggg cagtagggcg gcttcttcgt  3720
ctagggcttg catttgggcg tgatctggt cttagcgtg tgaaagtgtg tcgtaggtgg  3780
cgtgctcaat gcactcgaac gtcacgtcat ttaccggctc acggtgggca aagaactca  3840
gtgggttaga cattgttttc ctcgttgtcg tgtggtggtga gcttttctag ccgctcggta  3900
aacgcggcga tcatgaactc ttggaggttt tcaccgttct gcatgcctgc gcgcttcatg  3960
tcctcacgta gtgccaaagg aacgcgtgcg gtgaccacga cgggcttagc ctttgcctgc  4020
gcttctagtg cttcgatggt ggcttgtgcc tgcgcttgct gcgcctgtag tgcctgttga  4080
gcttcttgtg ttgctgttc tagctgttgc ttggtgcca tgtcttaaga ctctagtagc  4140
tttcctgcga tatgtcatgc gcatgcgtag caaacattgt cctgcaactc attcattatg  4200
tgcagtgctc ctgttactag tcgtacatac tcatatttac ctagtctgca tgcagtgcat  4260
gcacatgcag tcatgtcgtg ctaatgtgta aaacatgtac atgcagattg ctggggtgc  4320
agggggcgga gccaccctgt ccatgcgggg tgtgggcctt gccccgccgg tacagacagt  4380
gagcaccggg gcacctagtc gcggataccc ccctaggta tcgacacgt aaccctccca  4440
```

```
tgtcgatgca aatctttaac attgagtacg ggtaagctgg cacgcatagc caagctaggc    4500
ggccaccaaa caccactaaa aattaatagt tcctagacaa gacaaacccc cgtgcgagct    4560
accaactcat atgcacgggg gccacataac ccgaaggggt ttcaattgac aaccatagca    4620
ctagctaaga caacgggcac aacacccgca caaactcgca ctgcgcaacc ccgcacaaca    4680
tcgggtctag gtaacactga aatagaagtg aacacctcta aggaaccgca ggtcaatgag    4740
ggttctaagg tcactcgcgc tagggcgtgg cgtaggcaaa acgtcatgta caagatcacc    4800
aatagtaagg ctctggcggg gtgccatagg tggcgcaggg acgaagctgt tgcggtgtcc    4860
tggtcgtcta acggtgcttc gcagtttgag ggtctgcaaa actctcactc tcgctggggg    4920
tcacctctgg ctgaattgga agtcatgggc gaacgccgca ttgagctggc tattgctact    4980
aagaatcact tggcgcgggg tggcgcgctc atgatgtttg tgggcactgt tcgacacaac    5040
cgctcacagt catttgcgca ggttgaagcg ggtattaaga ctgcgtactc ttcgatggtg    5100
aaaacatctc agtggaagaa agaacgtgca cggtacgggg tggagcacac ctatagtgac    5160
tatgaggtca cagactcttg ggcgaacggt tggcacttgc accgcaacat gctgttgttc    5220
ttggatcgtc cactgtctga cgatgaactc aaggcgtttg aggattccat gttttcccgc    5280
tggtctgctg gtgtggttaa ggccggtatg gacgcgccac tgcgtgagca cgggggtcaaa    5340
cttgatcagg tgtctacctg gggtggagac gctgcgaaaa tggcaaccta cctcgctaag    5400
ggcatgtctc aggaactgac tggctccgct actaaaaccg cgtctaaggg gtcgtacacg    5460
ccgtttcaga tgttggatat gttggccgat caaagcgacg ccggcgagga tatggacgct    5520
gttttggtgg ctcggtggcg tgagtatgag gttggttcta aaaacctgcg ttcgtcctgg    5580
tcacgtgggg ctaagcgtgc tttgggcatt gattacatag acgctgatgt acgtcgtgaa    5640
atggaagaag aactgtacaa gctcgccggt ctggaagcac cggaacgggt cgaatcaacc    5700
cgcgttgctg ttgctttggt gaagcccgat gattggaaac tgattcagtc tgatttcgcg    5760
gttaggcagt acgttctaga ttgcgtggat aaggctaagg acgtggccgc tgcgcaacgt    5820
gtcgctaatg aggtgctggc aagtctgggt gtggattcca ccccgtgcat gatcgttatg    5880
gatgatgtgc acttggacgc ggttctgcct actcatgggg acgctactaa gcgtgatctg    5940
aatgcggcg tgttcgcggg taatgagcag actattcttc gcacccacta aaagcggcat    6000
aaacccccgtt cgatattttg tgcgatgaat ttatggtcaa tgtcgcgggg gcaaactatg    6060
atgggtcttg ttgttgacaa tggctgattt catcaggaat ggaactgtca tgctgttatg    6120
tgcctggctc ctaatcaaag ctgggggacaa tgggttgccc cgttgatctg atctagttcg    6180
gattggggg gcttcactgt atctgggggt ggcatcgtga atagattgca caccgtagtg    6240
ggcagtgtgc acaccatagt ggccatgagc accaccaccc caggggacgc cgacggcgcg    6300
aagctctgcg cctggtgcgg ctcggagatc aagcaatccg cgctcggccg gagcggggac    6360
tactgccgcc gctcctgccg ccagcgggcg tacgaggccc ggcgcagcg cgaggcgatc    6420
gtgtccgccg tggcgtcggc agtcgctcgc cgagatacgt cacgtgacga aatgcagcag    6480
ccttccattc cgtcacgtga cgaaactcgg gccgcaggtc agagcacggt tccgcccgct    6540
ccggccctgc cggaccccgg gcatcccgca agaggcccgg cagtaccggc ataaccaagc    6600
ctatgcctac agcatccagg gtgacggtgc cgaggatgac gatgagcgca ttgttagatt    6660
tcatacacgg tgcctgactg cgttagcaat ttaactgtga taaactaccg cattaaagct    6720
tatccgagtc caatgtgtcc gtgttcacct cagccggccgc accggtcggg gtaccttgac    6780
aaatactttc caatggggta caatggcgca gtgccatcca ctccgaggtt gataccagcc    6840
tcctcggtga aatgatcatc cgcgtcggag acgaagtaat tgacggcagc acctcggggga    6900
gacctcaaat ggtctcgcgt taacttaagg taccgaattc taagcttcac aaaaaaaaac    6960
cccgccctg acagggcggg gtttttttta ctcagcatgt ggatgccag tggtcggacc     7020
gagcgcttta attaattagc atggtgacac aagcacagta t                       7061

SEQ ID NO: 12           moltype = DNA   length = 1116
FEATURE                 Location/Qualifiers
source                  1..1116
                        mol_type = genomic DNA
                        organism = Mycobacterium tuberculosis
                        strain = Mycobacterium tuberculosis H37Ra
SEQUENCE: 12
atgcgcgtcg gtattccgac cgagaccaaa aacaacgaat tccgggtggc catcaccccg     60
gccggcgtcg cggaactaac ccgtcgtggc catgaggtgc tcatccaggc aggtgccgga    120
gagggctcgg ctatcaccga cgcggatttc aaggcggcag gcgcaact ggtcggcacc     180
gccgaccagg tgtgggccga cgctgattta ttgctcaagg tcaaagaacc gatagcggcg    240
gaatacggcc gcctgcgaca cgggcagatc ttgttcacgt tcttgcattt ggccgcgtca    300
cgtgcttgca ccgatgcgtt gttggattcc ggcaccacgt caattgccta cgagaccgtc    360
cagaccgccg acggcgcact accctgctt gccccgatga gcgaagtcgc cggtcgactc    420
gccgcccagg ttggcgctta ccacctgatg cgaacccaag ggggccgcgg tgtgctgatg    480
ggcggggtgc ccggcgtcga accggccgac gtcgtggtga tcggcgccgg caccgccggc    540
tacaacgcag cccgcatcgc caacggcatg ggcgcgaccg ttacgttct agacatcaac    600
atcgacaaac ttcggcaact cgacgccgag ttctgcggcc ggatccacac tcgctactca    660
tcggcctacg agctcgaggg tgccgtcaaa cgtgccgacg tgtgattgg ggccgtcctg    720
gtgccaggcg ccaaggcacc caaattagtc tcgaattcac ttgtcgcgca tatgaaacca    780
ggtgcggtac tggtggatat agccatcgac cagggcggct gtttcgaagg ctcacgaccg    840
accacctacg accacccgac gttcgccgtg cacgacacgc tgttttactg cgtggcgaac    900
atgcccgcct cggtgccgaa gacgtcgacc tacgcgctga ccaacgcgac gatgccgtat    960
gtgctcgagc ttgccgacca tggctggcgg gcggcgtgcc ggtcgaatcc ggcactagcc   1020
aaaggtcttt cgacgcacga aggggcgtta ctgtccgaac gggtggccac cgacctgggg   1080
gtgccgttca ccgagcccgc cagcgtgctg gcctga                             1116

SEQ ID NO: 13           moltype = AA   length = 371
FEATURE                 Location/Qualifiers
source                  1..371
                        mol_type = protein
                        note = strain: Mycobacterium tuberculosis H37Ra
                        organism = Mycobacterium tuberculosis
SEQUENCE:

```
MRVGIPTETK NNEFRVAITP AGVAELTRRG HEVLIQAGAG EGSAITDADF KAAGAQLVGT    60
ADQVWADADL LLKVKEPIAA EYGRLRHGQI LFTFLHLAAS RACTDALLDS GTTSIAYETV   120
QTADGALPLL APMSEVAGRL AAQVGAYHLM RTQGGRGVLM GGVPGVEPAD VVVIGAGTAG   180
YNAARIANGM GATVTVLDIN IDKLRQLDAE FCGRIHTRYS SAYELEGAVK RADLVIGAVL   240
VPGAKAPKLV SNSLVAHMKP GAVLVDIAID QGGCFEGSRP TTYDHPTFAV HDTLFYCVAN   300
MPASVPKTST YALTNATMPY VLELADHGWR AACRSNPALA KGLSTHEGAL LSERVATDLG   360
VPFTEPASVL A                                                       371

SEQ ID NO: 14           moltype = DNA  length = 1700
FEATURE                 Location/Qualifiers
source                  1..1700
                        mol_type = other DNA
                        organism = synthetic construct
SEQUENCE: 14
caactcggtc tctatccgag tccaatgtgt ccgtgttcac ctcagcggcc attgaagcct    60
aaaaacgacc gagccattg ggattaccat tgaagccagt gtgagttgca tcacattggc    120
ttcaaatctg agactttaat ttgtggattc acggggtgt aatgtagttc ataattaacc    180
ccattcgggg gagcagatcg tagtgcgaac gatttcaggt tcgttccctg caaaaactat    240
ttagcgcaag tgttgaaaat gccccgtt gggtcaatg tccattttg aatgtgtctg    300
tatgattttg catctgttgc caaatctttg tttccccgct ataattgagg acaggttgac    360
acggagttga ctcgacgaat tatccaatgt gagtaggttt ggtgcgtgag ttgaaaaaat    420
tcgccatact cgccctggg ttctgtcagc tcaagaattc ttgagtgacc gatgctctga    480
ttgacctaac tgcttgacac attgcatttc ctacaatcgc gagaggagac acaacatgcg    540
cgtgggtatc caaccgaaa ccaagaacaa cgagttccgc gtcgcaatca ccccagctgg    600
tgtcgctgag ctcaccccgcc gtggccacga agtactgatc caggcaggcg ccggtgaggg    660
ctccgccatc accgatgctg acttcaaagc agccggcgct caactggtcg gcaccgttgg    720
ccaggtgtgg gccgacgcag acctgctgct gaaggtcaaa gaaccatttg ccgcagaata    780
cggccgcctg cgccacggcc agatcctgtt caccttcctc cacctggcag cttcccgtgc    840
gtgcaccgac gctctgctgg actctggcac cacctcgatc gcttacgaga ctgtacagac    900
tgctgatggt gcactccac ttctcgcccc aatgtccgag gcaggcc gcctcgcagc    960
acaagttggc gcataccacc tgatgcgtac ccagggcgt cgcggagtcc tcatgggcgg    1020
agtccctggc gtcgaaccag ctgacgtcgt agtcatcgga gccggcaccg caggctacaa    1080
cgccgctcgt atcgcaaacg gcatgggtgc aaccgtcacc gtcctggaca ttaatatcga    1140
caagcttcgc cagctcgacg ctgaattctg cggtcgtatt cacaccgct actcctcga    1200
atatgaactt gagggcgctg tcaagcgtga tgacctggtt atcggcgcag tcctggttcc    1260
aggcgctaag caccaaagc tcgtgtccaa ctccctggtc gcacacatga agcctggcgc    1320
agtcctggtc gacatcgcta tcgaccaagg cggatgcttc gagggctccc gcccaaccac    1380
ctacgaccac ccaaccttcg ccgtgcacga cacccctcttc tactgtgttg caaacatgcc    1440
agcatccgtt ccaaagacct ccacatacgc tctcaccaac gcaaccatgc catacgttct    1500
ggaactggct gaccacggct ggcgcgctgc atgtcgctcc aaccctgccc tggcgaaggg    1560
tttgagtacc cacgagggtg cactcctgtc agaacgtgtc gcaaccgact ggcgttcc    1620
cttcaccgaa ccagcctccg tgctcgctta taagctcgg tacccgggga tccgacgtca    1680
ggaaaggaga gacccattga                                               1700

SEQ ID NO: 15           moltype = DNA  length = 1446
FEATURE                 Location/Qualifiers
source                  1..1446
                        mol_type = genomic DNA
                        organism = Arabidopsis thaliana
SEQUENCE: 15
atggctctca aggcattaga ctacgatact ctgaatgaaa acgtcaagaa gtgtcagtat    60
gccgtaagag gtgaactta tctccgagct tctgagctgc agaaagaagg caaaagatt    120
atttcacaa acgttgggaa ccctcatgct ttaggacaga agccattgac atttcctcgc    180
caggtggttc gctttgcca agctccgttt ctactagatg acccaaatgt ggaatgcta    240
tttccagctg atgctattgc aagagctaaa cattatcttt ccttgacttc aggcggttta    300
ggtgcttaca gtgattcaag aggccttcca ggagttagga agaggttgc tgagttcatt    360
caacggcgtg atgggtatcc aagtgaccca gaactcatct ttctcactga tggagctagc    420
aaaggtgtga tgcaaatctt gaattgtgtt atacgcggta atggagatgg gattctagtt    480
ccggttccac agtatccact ttactcagct accatatcac tgttaggtgg tactcttgtt    540
ccttactatc ttgatgagtc tgaaaactgg ggacttgatg ttgctaacct tcgacaatcc    600
gttgctcagg ctcgttctca agggataaca gtaagggcaa tggtgatcat taaccctggg    660
aacccaactg gccagtgtct aagcgaagct aacataagag agatattgaa gttcgttat    720
aacgagaaac tggttcttct gggagacgag gtttatcagc agaacatata ccaggatgag    780
cgtcccttta tcagctccaa gaaggttttg atggaaatgg gttcgcgtt cagcaaggaa    840
gttcagcttg tatctttca cacagtctct aaaggatatt ggggtgaatg tggacagcga    900
ggtggatact ttgagatgac caactccct ccaaggttg ttgaggagat atacaaggtt    960
gcatcaattg ccctcagccc taatgtctct gcgcaaatct ttatggggttt gatggttaat    1020
cctccaaagc ctggagacat ttcatatgac cagttcgccc gtgaaagcaa gggatattt    1080
gaatctttga gaagaagagc aaggctcatg acatgtggat tcaacagctg caaaaacgtc    1140
gtgtgcaatt tcacagaagg tgcaatgtat tcgtttcctc aaatacggtt accaacggga    1200
gctctccaag ctgcaaaaca agctggaaaa gtgccagacg ttttctactg tctcaagctc    1260
ttagaagcca caggaatctc cacagtacct ggctctggat ttgacagaa agaaggtgtg    1320
ttccatctga ggacaacaat cctgccagca gaagatgaga tgccggagat catggatagc    1380
ttcaagaagt tcaacgacga gttcatgact cagtatgata taactttgg ttattcgaaa    1440
atgtga                                                              1446

SEQ ID NO: 16           moltype = AA  length = 481
FEATURE                 Location/Qualifiers
source                  1..481
```

```
                        mol_type = protein
                        organism = Arabidopsis thaliana
SEQUENCE: 16
MALKALDYDT LNENVKKCQY AVRGELYLRA SELQKEGKKI IFTNVGNPHA LGQKPLTFPR     60
QVVALCQAPF LLDDPNVGML FPADAIARAK HYLSLTSGGL GAYSDSRGLP GVRKEVAEFI    120
QRRDGYPSDP ELIFLTDGAS KGVMQILNCV IRGNGDGILV PVPQYPLYSA TISLLGGTLV    180
PYYLDESENW GLDVANLRQS VAQARSQGIT VRAMVIINPG NPTGQCLSEA NIREILKFCY    240
NEKLVLLGDE VYQQNIYQDE RPFISSKKVL MEMGSPFSKE VQLVSFHTVS KGYWGECGQR    300
GGYFEMTNLP PRVVEEIYKV ASIALSPNVS AQIFMGLMVN PPKPGDISYD QFARESKGIL    360
ESLRRRARLM TDGFNSCKNV VCNFTEGAMY SFPQIRLPTG ALQAAKQAGK VPDVFYCLKL    420
LEATGISTVP GSGFGQKEGV FHLRTTILPA EDEMPEIMDS FKKFNDEFMT QYDNNFGYSK    480
M                                                                    481

SEQ ID NO: 17           moltype = DNA   length = 1548
FEATURE                 Location/Qualifiers
source                  1..1548
                        mol_type = other DNA
                        organism = synthetic construct
SEQUENCE: 17
caactcggtc tcgctcggta cccggggatc gacgtcagga aaggagagg attgatggct      60
ctgaaggctc tcgattacga cacccctgaac gagaacgtca agaagtgcca gtacgctgtg  120
cgcggcgagc tgtaccttcg tgcttccgag ctgcagaagg agggcaagaa gattattttc   180
accaacgtag gcaaccctca cgctctgggc cagaagccac ttaccttccc acgccaggtt   240
gttgctcttt gccaggcacc attcctgctg gatgatccta acgtaggtat gctgttccca   300
gctgacgcta ttgctcgcgc taagcactac ctgtctctga cttccggtgg tcttggcgct   360
tactccgatt cccgcggcct gccaggtgtc cgcaaggagg tggctgagtt cattcagcgc   420
cgcgacggct acccatccga ccctgaactc atcttcctta ccgatggtgc ttctaagggt   480
gtaatgcaga ttctcaactg tgtgattcgc ggtaacggcg atggtatcct tgtcccagtc   540
ccacagtacc cactgtactc cgctactatt tctcttctcg gcggcaccct ggttccatac   600
tacctggacg aatccgagaa ctggggcctc gacgtagcta accttcgtca gtccgtacgc   660
caggctcgtt cccagggcat cactgtccgc gctatggtta ttattaaccc aggcaaccca   720
actggccagt gcctgtccga agcaaacatt cgtgagatcc ttaagttctg ctacaacgag   780
aagctggtac tcttaggcga cgaggtatac cagcagaaca tttaccagga tgaacgccct   840
ttcatctcct ccaagaaggt actgatggag atgggctcgc cattctccaa ggaagttcag   900
ctggttttcct tccacactgt ctctaagggt tactgggtgg aatgtggcca gcgcggcggc   960
tacttcgaaa tgactaacct cccacctcgc gtcgtggaag agatctacaa ggttgcatct  1020
attgctctgt ccccaaacgt atccgctcag atcttcatgg gctgatggt aaacccacct  1080
aagcctggcg acatttccta cgaccagttc gctcgtgaat ctaagggtat ccttgaatcc  1140
cttcgtcgcc gcgctcgtct gatgactgac ggcttcaact cctgtaagaa ctagtatgcc  1200
aacttcaccg aaggcgctat gtactctttc ccacagatcc gtcttccaac cggtgcactc  1260
caggctgcta agcaggctgg caaggtgcca gatgtgttct actgtctcaa gctgctggag  1320
gctaccggca tctccactgt tccaggctcc ggcttcggcc agaaggaggg cgttttccac  1380
ctgcgtacca ctatccttcc tgctgaggat gagatgcctg aaattatgga ttctttcaag  1440
aagttcaacg acgagttcat gactcagtac gacaacaact tcggctactc caagatgtaa  1500
taaggccgca ccggtcgggg taccttgaca aatactgaga cccattga                1548

SEQ ID NO: 18           moltype = DNA   length = 156
FEATURE                 Location/Qualifiers
source                  1..156
                        mol_type = other DNA
                        organism = synthetic construct
SEQUENCE: 18
gctcggtacc cggggatccg acgtcaggaa aggagaggat tgatgaattc aggtatctcg      60
gagatcgcga gagctcgtaa ctgcgacgga cacctaatgc cctttagtac caaatggggg    120
agttaataag gccgcaccgg tcggggtacc ttgaca                              156

SEQ ID NO: 19           moltype = AA    length = 481
FEATURE                 Location/Qualifiers
source                  1..481
                        mol_type = protein
                        organism = Arabidopsis thaliana
SEQUENCE: 19
MSLKALDYES LNENVKNCQY AVRGELYLRA SELQKEGKKI IFTNVGNPHA LGQKPLTFPR      60
QVVSLCQAPF LLDDPNVGMI FPADAIARAK HYLSLTSGGL GAYSDSRGLP GVRKEVAEFI    120
ERRDGYPSDP ELIFLTDGAS KGVMQILNCV IRGKDGILV PVPQYPLYSA TISLLGGTLV     180
PYYLEESENW GLDVNNLRQS VAQARSQGIT VRAMVIINPG NPTGQCLSEA NIRELRFCC     240
DERLVLLGDE VYQQNIYQDE RPFISSKKVL MDMGAPISKE VQLISFHTVS KGYWGECGQR    300
GGYFEMTNIP PRTVEEIYKV ASIALSPNVS AQIFMGLMVN PPKPGDISYD QFVRESKGIL    360
ESLRRRARMM TDGFNSCKNV VCNFTEGAMY SFPQIKLPSK AIQAAKQAGK VPDVFYCLKL    420
LEATGISTVP GSGFGQKEGV FHLRTTILPA EEEMPEIMDS FKKFNDEFMS QYADNFGYSR    480
M                                                                    481

SEQ ID NO: 20           moltype = AA    length = 407
FEATURE                 Location/Qualifiers
source                  1..407
                        mol_type = protein
                        organism = Thermococcus litoralis
SEQUENCE: 20
MDYTKYLAGR ANWIKGSALA DVMKKASELQ KKGVKLISLA AGDPDPELIP RAVLGEIAKE     60
```

```
VLEKEPKSVM YTPANGIPEL REELAAFLKK YDHLEVSPEN IVITIGGTGA LDLLGRVLID    120
PGDVVITENP SYINTLLAFE QLGAKIEGVP VDNDGMRVDL LEEKIKELKA KGQKVKLIYT    180
IPTGQNPMGV TMSMERRKAL LEIASKYDLL IIEDTAYNFM RYEGGDIVPL KALDNEGRVI    240
VAGTLSKVLG TGFRIGWIIA EGEILKKVLM QKQPIDFCAP AISQYIALEY LKRGYFEKYH    300
LEGALLGYKE KRDIMLKALE NHLPNAEFTK PIAGMFVMFF LPEGADGISF ANELMEREGV    360
VVVPGKPFYT DESGKNAIRL NFSRPSKEEI PIGIKKLAKL YKEKFGE                 407

SEQ ID NO: 21          moltype = AA  length = 371
FEATURE                Location/Qualifiers
source                 1..371
                       mol_type = protein
                       note = strain: Mycolicibacterium smegmatis MC2 155
                       organism = Mycolicibacterium smegmatis
SEQUENCE: 21
MLVGIPTEIK NNEYRVAITP AGVAELTRRG HEVIIQAGAG EGSAISDRDF KAAGAEIVNT     60
ADQVWSEAEL LLKVKEPIEP EYSRMRKGQT LFTYLHLAAS KPCTDALLAS GTTSIAYETV    120
QTAEGALPLL APMSEVAGRL SAQVGAYHLM RSYGGRGVLM GGVPGVAPAE VVVIGAGTAG    180
YNAARVAAGM GAHVTVFDLN INTLRRVDGE FGGRIETRYS SSLELEEAVK KADLVIGAVL    240
VPGAKAPKLV TNSTVAHMKP GAVLVDIAID QGGCFEDSRP TTHDEPTFKV HDTIFYCVAN    300
MPGAVPRTST FALTNSTMPY VLKLADKGWQ AACASDSALA KGLSTHDGKL LSEAVAKDLD    360
LPFTDAAQFL A                                                        371

SEQ ID NO: 22          moltype = AA  length = 378
FEATURE                Location/Qualifiers
source                 1..378
                       mol_type = protein
                       note = subspecies and strain: Bacillus subtilis subsp.
                        subtilis str. 168
                       organism = Bacillus subtilis
SEQUENCE: 22
MIIGVPKEIK NNENRVALTP GGVSQLISNG HRVLVETGAG LGSGFENEAY ESAGAEIIAD     60
PKQVWDAEMV MKVKEPLPEE YVYFRKGLVL FTYLHLAAEP ELAQALKDKG VTAIAYETVS    120
EGRTLPLLTP MSEVAGRMAA QIGAQFLEKP KGGKGILLAG VPGVSRGKVT IIGGGVVGTN    180
AAKMAVGLGA DVTIIDLNAD RLRQLDDIFG HQIKTLISNP VNIADAVAEA DLLICAVLIP    240
GAKAPTLVTE EMVKQMKPGS VIVDVAIDQG GIVETVDHIT THDQPTYEKH GVVHYAVANM    300
PGAVPRTSTI ALTNVTVPYA LQIANKGAVK ALADNTALRA GLNTANGHVT YEAVARDLGY    360
EYVPAEKALQ DESSVAGA                                                 378

SEQ ID NO: 23          moltype = AA  length = 371
FEATURE                Location/Qualifiers
source                 1..371
                       mol_type = protein
                       note = strain: Streptomyces fradiae ATCC 10745 = DSM 40063
                       organism = Streptomyces fradiae
SEQUENCE: 23
MKVGIPREVK NNEFRVAITP AGVHELVRNG HQVFVEQNAG VGSSITDDEY VAAGARILPT     60
ADEVWATADL LLKVKEPIAE EYHRLRKDQT LFTYLHLAAS RECTDALLAS GTTAIAYETV    120
ETANRALPLL APMSEVAGRL APQVGAYHLM RANGGRGVLP GGVPGVVPAK AVVIGGGVSG    180
WNATQIAVGM GFDVTLLDRD INKLREADKI FGTKVKAVMS NSFELEKAVL DADLVIGAVL    240
IPGAKAPKLV TNELVSRMKP GSVLVDIAID QGGCFEDSRP TTHADPSFPV HESIFYCVAN    300
MPGAVPNTST YALTNATLPY IVSLANNGWV EALRRDPALA KGLNTHDGKV VYRQVAEAHG    360
LDHVELASLI G                                                        371

SEQ ID NO: 24          moltype = AA  length = 360
FEATURE                Location/Qualifiers
source                 1..360
                       mol_type = protein
                       note = strain: Aphanothece halophytica CM1
                       organism = Aphanothece halophytica
SEQUENCE: 24
MEIGVPKETK DQEYRVGLSP SSVRSLCERK HPVFVETQAG VGAGFSDQDY EAAGATVVPD     60
PKSAWNRELV VKVKEPLPDE YTYLQKNQVL FTYLHLAANR RLTEALIDSG ISAIAYETVE    120
LPNGKLPLLN PMSIIAGRLS VQFGARYLEK QQGGRGVLLG GFPGVRSGRV VILGGGVVGT    180
EAARMAVGIG AQVQILDVNV ERLAELENLF GSRVELLYSN SSQIEAVVPE ADLLIGAVLT    240
TGKRAPKLVT RELVKQMRAG SVIVDVAVDQ GGCVETLQVT SHSHPTYTEE GVVHFGVPNM    300
PGAVPWTATQ ALNNSTLPYV IQLADQGLTA LESNPILGKG LNVQKQQLIH PAVKEVFPDL    360
```